United States Patent [19]

Seubert et al.

[11] 4,051,243

[45] Sept. 27, 1977

[54] RING SUBSTITUTED PYRAZINO-ISOQUINOLINE DERIVATIVES AND THEIR PREPARATION

[75] Inventors: Jürgen Seubert; Rolf Pohlke, both of Darmstadt; Herbert Thomas; Peter Andrews, both of Wuppertal, all of Germany

[73] Assignee: Merck Patent Gesellschaft mit beschrankter Haftung, Darmstadt, Germany

[21] Appl. No.: 607,810

[22] Filed: Aug. 26, 1975

[30] Foreign Application Priority Data

Aug. 28, 1974 Germany .............................. 2441261

[51] Int. Cl.$^2$ .................. C07D 241/36; A61K 31/495
[52] U.S. Cl. ............................ 424/250; 260/250 BC; 260/268 TR; 260/268 MK; 260/288 A
[58] Field of Search .................. 260/268 TR; 424/250

[56] References Cited

U.S. PATENT DOCUMENTS 4,001,411 1/1977 Seubert et al. ................ 260/268 TR Primary Examiner—Donald G. Daus
Assistant Examiner—Jose Tovar Attorney, Agent, or Firm—Millen & White

[57] ABSTRACT

Isoquinolines of the formula

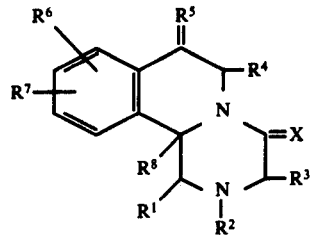

wherein $R^1$ is H, OH, alkyl; $R^2$ is H, or an unsubstituted or substituted carbonyl, carbonyloxy or thiocarbonyl group; $R^3$ is H, alkyl or hydroxy alkyl; $R^4$ is H, alkyl or phenyl; $R^5$ is O, H,H or H and alkyl, phenyl, halo or hydroxy; $R^6$ and $R^7$ are optional substituents; and $R^8$ is H or alkyl, $R^2$ being a thiocarbonyl or carbonyloxy group when $R^1$ and $R^3$ to $R^8$ are H and X is O; and their physiologically acceptable salts, are antihelmintics, especially against cestodes and trematodes; some also possessing CNS activity, e.g., psychotropic and blood pressure regulating activity.

22 Claims, No Drawings

RING SUBSTITUTED PYRAZINO-ISOQUINOLINE DERIVATIVES AND THEIR PREPARATION

BACKGROUND OF THE INVENTION

This invention relates to novel ring-substituted 4-oxo- and 4-thioxo-hexahydro-4H-pyrazino-[2,1-a]isoquinoline derivatives and their preparation. Similar compounds are described in German Offenlegungsschrift No. 1,470,062 and in U.S. Pat. No. application Ser. No. 533,467, now U.S.Pat. No. 4,001,411 granted Jan. 4, 1977.

SUMMARY OF THE INVENTION

The novel isoquinoline derivatives of this invention are compounds of the general Formula I:

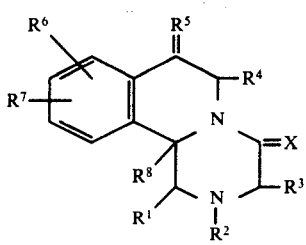

wherein $R^1$ is a hydrogen atom, hydroxy or alkyl; $R^2$ is a hydrogen atom or $CYR^9$; $R^3$ is a hydrogen atom, alkyl or hydroxyalkyl; $R^4$ is a hydrogen atom, alkyl or phenyl; $R^5$ is an oxygen atom, two hydrogen atoms, or a hydrogen atom and one of alkyl, phenyl, halogen atom, or hydroxy; $R^6$ and $R^7$, which can be alike or different, each are a hydrogen atom, a halogen atom, hydroxy, amino, nitro, cyano, alkyl, alkoxy, acyloxy, monoalkylamino, dialkylamino, acylamino, benzoyloxy or the group Z; $R^8$ is a hydrogen atom or alkyl; $R^9$ is a hydrogen atom, alkyl of up to 6 carbon atoms or cycloalkyl or cycloalkenyl of 5 to 7 carbon atoms which is unsubstituted or substituted by oxygen or mono- or disubstituted by $R^{10}$ and can be interrupted in the ring by an oxygen atom, a sulfur atom, SO or $SO_2$, or is phenyl which is unsubstituted or mono- or disubstituted by $R^{10}$ or Z, or is thienyl, pyridyl or $R^{11}$; $R^{10}$ is a fluorine or chlorine atom, hydroxy, nitro, amino, monoalkylamino, dialkylamino or acylamino; $R^{11}$ is alkoxy, phenoxy or a cycloalkoxy of 5 to 7 carbon atoms, Hal is a fluorine, chlorine, bromine or iodine atom, X and Y, which can be the same or different, each is an oxygen or sulfur atom; Z is phenylazo or naphthylazo which is unsubstituted or substituted by one or more of halogen, hydroxyl, amino, alkyl, alkoxy, monoalkylamino, dialkylamino, COOH and $SO_3H$; alkyl, hydroxyalkyl, alkoxy and acyl unless otherwise indicated being up to 4 carbon atoms; with the proviso that $R^2$ is $CSR^9$ or $COR^{11}$ when $R^1$ and $R^3$ to $R^8$, inclusive, each are hydrogen atoms and X is an oxygen atom; and the physiologically acceptable salts thereof.

In a composition aspect, this invention relates to such novel isoquinolines. In another composition aspect, this invention relates to a pharmaceutical composition comprising in unit dosage form an antihelmintically effective amount of a novel isoquinoline of this invention in admixture with a pharmaceutically acceptable carrier.

In process aspects, this invention relates to processes for the production and use of such compositions.

DETAILED DESCRIPTION

The novel compounds of general Formula I and their physiologically acceptable salts possess, with good compatibility, valuable parasitological and other pharmaceutical activities. Thus, they are, inter alia, valuable anthelmintics and exhibit, in particular, a broad spectrum of activity against cestodes and trematodes. Some of the new compounds exhibit in activity upon the central nervous system and, in particular, possess psychotropic as well as blood pressure-influencing and especially blood pressure-lowering activities.

Additionally, some of the new compounds possess tranquilizing, adrenolytic and muscle-relaxant activities, which can be ascertained by conventional methods known for this purpose. These activities have been determined, for example, in mice, rats and rhesus monkeys.

The novel compounds of general Formula I and the physiologically compatible salts thereof can be used as pharmaceuticals in human and veterinary medicine, especially as anthelmintics, and also as intermediates for the preparation of other pharmaceuticals.

The alkyl, hydroxyalkyl, alkoxy and acyl values for $R^1$ through $R^{11}$ and Z each are of up to 4 carbon atoms unless otherwise indicated, but preferably they contain 1 or 2 carbon atoms. Thus, alkyl preferably is methyl, but also can be ethyl, as well as n-propyl, isopropyl, n-butyl, isobutyl, sec.-butyl and tert.-butyl. Hydroxyalkyl is preferably hydroxymethyl or 2-hydroxyethyl. Alkoxy is preferably methoxy, but can also be ethoxy, as well as n-propoxy, isopropoxy, n-butoxy, isobutoxy, sec.-butoxy and tert.-butoxy. Acyl is preferably acetyl but can also be formyl, propionyl, n-butyryl and isobutyryl. The same also applies to the groups derived from these radicals. Thus, monoalkylamino is preferably methylamino, dialkylamino is preferably dimethylamino or diethylamino, acylamino is preferably acetylamino and acyloxy is preferably acetoxy.

In $R^9$, alkyl can be of up to 6 carbon atoms and, in addition to the above-mentioned values, can also be, for example, straight-chained or branched pentyl and hexyl.

$R^1$ preferably is a hydrogen atom, hydroxy or methyl. $R^2$ is preferably $CYR^9$ but the compounds in which $R^2$ is a hydrogen atom are also of importance. $R^3$ is preferably a hydrogen atom, methyl or 2-hydroxyethyl. $R^4$ is preferably a hydrogen atom or methyl. $R^5$ preferably stands for two hydrogen atoms or for one hydrogen atom and a methyl group. At least one of $R^6$ and $R^7$ is preferably a hydrogen atom; other preferred values being fluorine, chlorine, bromine, hydroxy, amino, nitro, methyl and methoxy. $R^8$ preferably is a hydrogen atom or methyl.

$R^9$ preferably is unsubstituted or substituted cycloalkyl of 5 or 6 carbon atoms, especially unsubstituted or substituted cyclohexyl, as well as unsubstituted or substituted phenyl. Especially preferred substituents on the cycloalkyl radical are oxygen, for example, in the form of a keto group, fluorine atoms, nitro, amino, methylamino, dimethylamino and acetylamino radicals, as well as chlorine atoms, ethylamino, diethylamino, formylamino and propionylamino. Preferred substituents on the phenyl radical are fluorine atoms, amino, nitro, methylamino, dimethylamino, formylamino and acetylamino, which are preferably in the m or p-position but can also be in the o-position. Examples of other substituents on the phenyl radical are chlorine atoms, hydroxy, ethylamino, diethylamino, n-propylamino, propionylamino, n-butyrylamino and isobutyrylamino, which are preferably in the m- or p-position but can also be in the o-position. Other preferred values for $R^9$ are 2- or 3-cyclohexenyl, thienyl attached at the 2- or 3-position, pyridyl attached at the 2-, 3- or 4-position, tetrahydropyranyl attached at the 2-, 3- or 4-position, thiacyclohexyl attached at the 2-, 3- or 4-position, which can be mono- or disubstituted on the sulfur atom by oxygen (especially thiacyclohexyl-4), cyclohexadienyl or $R^{11}$. $R^9$ can also be, for example, alkyl of up to 6 carbon atoms, cyclopentyl, cycloheptyl, 2- or 3-cyclopentenyl or 2-, 3- or 4-cycloheptenyl.

$R^{10}$ is a fluorine atom, amino, methylamino, dimethylamino, formylamino, acetylamino or nitro. $R^{11}$ preferably is methoxy or cyclohexyloxy. Hal is preferably fluorine and chlorine. Z preferably is 4-hydroxyphenylazo, 4-methoxyphenylazo, 4-aminophenylazo, 4-methylaminophenylazo, 4-dimethylaminophenylazo, naphthyl-1-azo or naphthyl-2-azo unsubstituted or substituted in the 1- or 2-, 4-, 6-, 7-, 8-, or 9-position by hydroxy, alkoxy, amino, alkylamino, dialkylamino, COOH or $SO_3H$.

Preferred compounds of this invention are, in particular, those of general Formula I and their acid addition salts in which at least one of these symbols has one of the above-given preferred values. Some of these preferred groups of compounds can be defined by the following part Formulae Ia to Is, which otherwise correspond to the above-given general Formula I but wherein:

Ia: $R^1$ is hydrogen;
Ib: $R^2$ is hydrogen;
Ic: $R^2$ is $COR^9$;
Id: $R^2$ is CS-alkyl, CS-cycloalkyl containing 5 or 6 carbon atoms or thiobenzoyl;
Ie: $R^3$ is hydrogen;
If: $R^4$ is hydrogen or methyl;
Ig: $R^5$ represents two hydrogen atoms or a hydrogen atom and methyl group;
Ih: $R^6$ and $R^7$ are hydrogen;
Ii: $R^8$ is hydrogen;
Ij: $R^1$, $R^3$, $R^6$ to $R^8$ each are hydrogen;
Ik: $R^1$ and $R^3$ to $R^8$ each are hydrogen and X is sulfur;
Il: $R^2$ is $COR^9$ wherein $R^9$ is alkyl or up to 4 carbon atoms, cyclohexyl which is either unsubstituted or is substituted by an oxygen atom, one or two fluorine atoms, methylamino or dimethylamino, or phenyl which is either unsubstituted or substituted in the m or p-position by fluorine, amino, methylamino or dimethylamino, or tetrahydropyranyl or thiacyclohexyl attached at the 2- or 4-position;
Im: $R^2$ is $COR^9$, $R^4$ is methyl and $R^9$ is phenyl, cyclohexyl, tetrahydropyranyl or thiacyclohexyl;
In: $R^2$ is $COR^9$, $R^5$ is methyl and $R^9$ is phenyl, cyclohexyl, tetrahydropyranyl or thiacyclohexyl;
Io: $R^2$ is $COR^9$, $R^4$ or $R^5$ is methyl and $R^9$ is phenyl or cyclohexyl substituted by nitro, amino or flurorine in the 3- or 4-position;
Ip: $R^1$ is hydrogen or hydroxy, $R^2$ is $CYR^9$, $R^3$ is hydrogen, methyl or 2-hydroxyethyl, $R^4$ is hydrogen or methyl, $R^5$ represents two hydrogen atoms or a hydrogen atom and a methyl group, one of $R^6$ and $R^7$ is hydrogen, hydroxy or methoxy and the other is hydrogen, hydroxy, amino, nitro, chlorine, methyl or methoxy, $R^8$ is hydrogen, $R^9$ is alkyl of up to 3 carbon atoms, cyclohexyl, oxocyclohexyl, tetrahydropyranyl, thiacyclohexyl, phenyl, fluorophenyl, aminophenyl, nitrophenyl, pyridyl, ethoxy, cycloexyloxy or phenoxy and X and Y, which can be alike or different, are oxygen or sulfur atoms;
Iq: $R^1$ is hydrogen, $R^2$ is $CYR^9$, $R^3$ is hydrogen or methyl, $R^4$ is hydrogen or methyl, $R^5$ represents two hydrogen atoms, or a hydrogen atom and a methyl group, one of $R^6$ and $R^7$ is hydrogen and the other is hydrogen, amino, nitro or chlorine, $R^8$ is hydrogen, $R^9$ is alkyl of up to 3 carbon atoms, cyclohexyl, phenyl, fluorophenyl, aminophenyl, nitrophenyl or pyridyl and X and Y, which can be alike or different, are oxygen or sulfur atoms;
Ir: $R^1$ is methyl; and
Is: $R^2$ is thiacyclohexyl-4-carbonyl.

In a process aspect, this invention relates to processes for the production of compounds of general Formula I, and their physiologically acceptable salts, wherein
a. a compound of the general Formula $$Q-R_2 \qquad (II)$$

wherein Q is

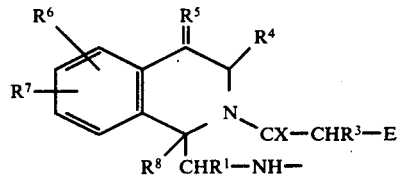

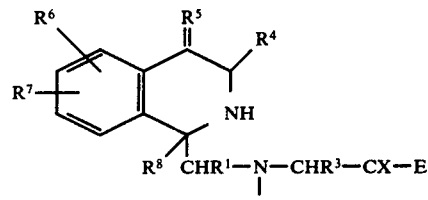

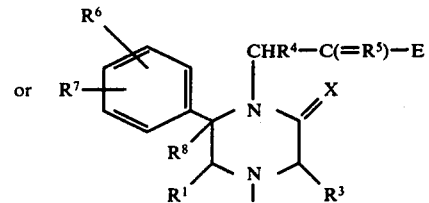

wherein E is a halogen atom, a hydroxy or a functionally modified hydroxy, and $R^1$ to $R^8$, Hal and X have the values given for general Formula I, is cyclized under conditions splitting off HE; or b. a compound of the general Formula III

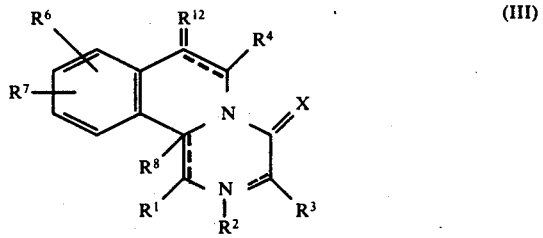

wherein $R^{12}$ has the same values as $R^5$ or is alkylidene of up to 4 carbon atoms and $R^1$ to $R^8$, X and Hal have the same values as given for general Formula I and the dotted lines mean that at one or more of these positions, a double bond can be present, with the proviso that $R^{12}$ is alkylidene when none thereof is a double bond, or a salt of said compound, is treated with a reducing agent; or c. a compound of the general Formula IV:

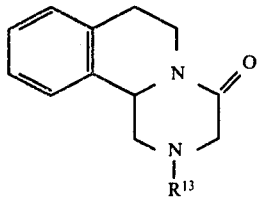

(IV)

wherein $R^{13}$ is a hydrogen atom or $COR^{14}$, $R^{14}$ is a hydrogen atom, alkyl of up to 6 carbon atoms or a cycloalkyl or cycloalkenyl of 5 to 7 carbon atoms which is either unsubstituted or is mono- or disubstituted by oxygen or by $R^{10}$ and/or interrupted in the ring by an oxygen atom or sulfur atom, $SO$ or $SO_2$ or is phenyl which is either unsubstituted or is mono- or disubstituted by $R^{10}$ or Z, or is thienyl, pyridyl, and $R^{10}$ and Z have the values given for Formula I, is treated with a hydroxylating, hydroxyalkylating, halogenating or nitrating agent or with an agent giving off sulfur; or d. a compound of general Formula IV wherein $R^{13}$ is a hydrogen atom, is treated with a thioacylating agent or with a compound of the general formula $R^{11}$—CO—E, wherein $R^{11}$ and E have the values given above; and, if desired, in the thus-obtained product, one or more of $R^1$ to $R^8$ and X are converted into another value thereof; and/or when the product obtained is a racemic compound, it is resolved into its optical antipodes and/or a compound in free base form is converted into a physiologically acceptable salt thereof with an acid or a base or into a quaternary ammonium salt and/or a free base of general Formula I is liberated from a thus-obtained acid addition salt thereof.

Otherwise, the above-described preparation of the compounds of this invention is achieved in a known manner by known methods, such as are described in the literature (for example in standard reference works, such as Houben-Weyl, Methoden der organischen Chemie, pub. Georg Thieme Verlag, Stuttgart), namely, under the reaction conditions which are known and are suitable for the said reactions.

If desired, the starting materials used for the preparation of the compounds of general Formula I can be formed in situ in such a manner that they are not isolated from the reaction mixture but are immediately further reacted to give the desired compounds of Formula I.

More particularly, for the preparation of compounds of general Formula I by cyclization, there can be used compounds of the following general formulae:

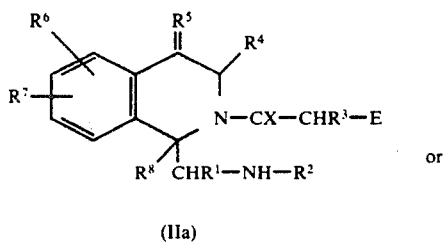

(IIa)

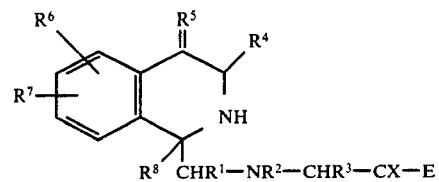

(IIb)

or 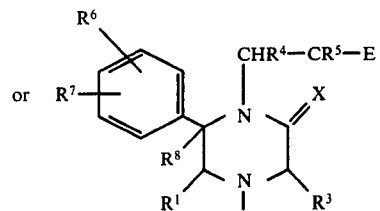

(IIc)

wherein $R^1$ to $R^8$, X and E have the values given above. The tetrahydroisoquinoline derivatives IIa and IIb are preferably used for the cyclization.

In general Formulae II, IIa, IIb and IIc, E is a group which is eliminated by the reaction. Therefore, the nature of this substituent is not critical. E is preferably a chlorine or bromine atom or hydroxy. E can also be a fluorine or iodine atom or an esterified hydroxy group, especially a reactively esterified hydroxy group, for example, an alkylsulfonyloxy, preferably of up to 6 carbon atoms, such as methanesulfonyloxy, arylsulfonyloxy, preferably of 6 to 10 carbon atoms, e.g., a benzenesulfonyloxy, p-toluene-sulfonyloxy or 1- or 2-naphthalenesulfonyloxy, or acyloxy, especially alkanoyloxy, preferably of up to 7 carbon atoms, e.g., acetoxy or heptanoyloxy, or benzoyloxy, as well as an ether group which can easily be split off, e.g., tetrahydropyranyl-2-oxy or, if E is part of an ester (Formula IIb or Formula IIc, if $R^5$ is oxygen), can also be alkoxy, preferably of up to 4 carbon atoms, more preferably methoxy or ethoxy.

More particularly, E in compounds of general Formula IIa is preferably a chlorine, bromine or iodine atom or one of the above-mentioned sulfonic acid ester radicals, preferably a p-toluene-sulfonyloxy. In compounds of general Formula IIb, E is preferably hydroxy, or alkoxy or acyloxy of up to 4 carbon atoms or a halogen atom. In compounds of general Formula IIc, E is preferably hydroxy or a halogen atom.

The compounds of general Formula II are cyclized in the presence or absence of a catalyst and preferably of a basic or acidic catalyst, as well as in the presence or absence of an additional inert solvent, at a temperature of from about $-20°$ to $+300°$ C.

The choice of the catalysts to be employed depends essentially upon the constitution of the starting material and of the compound HE to be split off. More particularly, as bases there can be used, for example, alkali metal or alkaline earth metal hydroxides, such as sodium, potassium, barium or calcium hydroxides, alkali metal or alkaline earth metal carbonates, such as sodium or potassium carbonates, alkali metal or alkaline earth metal bicarbonates, such as sodium or potassium bicarbonate, alkali metal or alkaline earth metal hydrides, such as sodium or potassium hydride, alkali metal or alkaline earth metal amides such as sodamide, potassamide or lithium, sodium or potassium piperidide or diisopropylamide, or alkali metal or alkaline earth metal alcoholates, such as sodium or potassium methylate, sodium or potassium ethylate or potassium tert.-butylate, organolkali metal compounds, such as butyl lithium, phenyl lithium or naphthyl sodium, as well as the alkali metal salts of weak acids, such as sodium acetate, and also ammonia and primary, secondary and, in particular, tertiary amines, such as triethylamine, dimethylaniline or pyridine and quanternary bases, such as benzyl trimethyl ammonium hydroxide. As acids, there can be used, for example, hydrohalic acids, such as hydrofluoric, hydrochloric or hydrobromic acid, sulfuric acid, phosphoric acid or polyphosphoric acid, as well as Lewis acids, such as aluminum trichloride, aluminum tribromide, boron trifluoride, zinc chloride, tin tetrachloride, gallium trichloride or gallium tribromide, and also inorganic acid halides, such as phosphorus trichloride, phosphorus pentachloride, thionyl chloride or phosphorus oxychloride, or agents splitting off water, for example carbodiimides, such as dicyclohexyl carbodiimide. The above-mentioned acids and Lewis acids are especially useful for the cyclization of compounds of general Formula IIc, which takes place according to the methods used for Friedel-Crafts alkylation or acylation.

As inert solvents, there can be used, for the cyclization of compounds of general Formulae IIa and IIb, especially alcohols, such as methanol, ethanol, isopropanol, n-butanol or tert.-butanol; ethers, such as diethyl ether, diisopropyl ether, tetrahydrofuran or dioxan; glycol ethers, such as ethylene glycol monomethyl or monoethyl ether (methyl glycol or ethyl glycol), ethylene glycol dimethyl ether (diglyme); ketones, such as acetone; amides, such as dimethylformamide or hexamethyl-phosphoric acid triamide; nitriles, such as acetonitrile; nitro compounds, such as nitromethane or nitrobenzene; sulfoxides, such as dimethyl sulfoxide; carbon disulfide; tertiary bases such as pyridine; chlorinated hydrocarbons, such as methylene chloride, chloroform or trichloroethylene; hydrocarbons, such as petroleum ether, hexane, benzene, toluene or xylenes. There can also be used mixtures of water with one of the above-mentioned alcohols, for example, 60% ethanol, as well as mixtures of water with acetone or dioxan. For the cyclization of compounds of general Formula IIc, it is preferred to use the solvents which are typical for Friedel-Crafts alkylations and acylations, such as petroleum ether, hexane, nitrbenzene or carrbon disulfide. These compounds can also be cyclized by the action of tertiary amines in high boiling alcohols, such as cyclohexanol.

More particularly, the compounds of general Formula IIa are preferably cyclized in the presence of strong bases, such as butyl lithium or potassium tert.-butylate, in polar solvents, such as tetrahydrofuran, dimethylformamide, hexamethyl phosphoric acid triamide or tert.-butanol, at temperatures of from about $-20°$ C. to $+200°$ C., reaction times of from about 15 minutes to about 30 hours usually being necessary. The cyclization of compounds of general Formula IIb takes place especially advantageously, in the absence of a solvent, by heating to temperatures of from about 140° to 250° C. and preferably of from 170° to 210° C., whereby it is possible to work at atmospheric pressure or also under reduced pressure. As catalysts for the cyclization of compounds of general Formula IIc, it is preferred to use hydrofluoric acid or aluminum trichloride, whereby there can be employed either an excess of the cyclization agent, such as hydrofluoric acid, as solvent or there can also be employed one of the above-mentioned additional inert solvents. Compounds of general Formulla IIc are preferably cyclized at a temperature of from about 0° to 150° C. and especially at a temperature of from 20° to 80° C.

It is also possible to cyclize a compound of general Formula II (E = OH) by first reacting it with, for example, thionyl chloride, optionally in the presence of a base, such as triethylamine or pyridine, to give the corresponding chloride of general Formula II (E = Cl) which is then allowed to react furthen in situ to give a compound of general Formula I.

The hexahydro-pyrazino-isoquinoline derivatives of general Formula I can also be obtained by reduction of compounds of general Formula III, preferably at a temperature of from about $-80°$ to $+250°$ C., in the presence of at least one inert solvent.

The compounds of general Formula III correspond to those of general Formula I except that, in addition, they contain in the IIb(1)- and/or 2(3)- and/or 6(7)-position, an additional double bond and/or instead of the radical $R^5$, in the 7-position there is present an alkylidene group of up to 4 carbon atoms, preferably a methylene or ethylidene. If an additional double bond is present in the 2(3)-position, then either radical $R^2$ is absent from compounds (III) or the compounds (III) are present in the form of a quaternary salt. Of the starting materials of general Formula III, preferred are those with a double bond in the IIb(1)-position.

Catalytic hydrogenation is preferably used for the reduction. As catalysts for the hydrogenation, there can be used, for example, a noble metals or nickel or cobalt catalysts, as well as mixed catalysts, such as copper-chromium oxide. As noble metals, there are preferably used platinum or palladium, which can be present on carriers such as charcoal, calcium carbonate or strontium carbonate, or as oxides or in finely-divided form. Nickel and cobalt catalysts are preferably employed as Raney metals. It is also possible to use complex compounds of heavy metals as catalysts, for example, soluble rhodium complexes, such as hydridocarbonyl-tris(-triphenylphosphine) rhodium. The hydrogenation can be carried out at pressures of from about 1 to 200 atms. and at temperatures of from anbout $-80°$ to $+200°$ C. and preferably at temperatures of from 20° to 100° C. The reaction can be carried out in an acidic, neutral or basic medium, preferably in the presence of one of the inert solvents already mentioned above or also in the presence of carboxylic acids, such as acetic acid, or of esters, such as ethyl acetate. The hydrogenation is preferably carried out on Raney nickel or with one of the above-metnioned platinum or palladium catalysts in an alcohol, such as methanol or ethanol, at ambient temperature and atmospheric pressure.

If, in the course of the reaction, new asymmetric centers arise, for example, of the $C_{(IIb)}$ atom, the reduction can also be directed in such a manner that one of the two possible antipodes of the compounds of general Formula I is formed exclusively or at least to a preponderant extent. This can take place, for example, by asymmetric hydrogenation in which, as catalysts, there can be used, for example, Raney nickel which is to be previously treated with an asymmetrical modifying reagent, for example, with a solution of an optically-active hydroxy or amino acid, such as tartaric acid, citric acid, alanine, isoleucine, lysine, phenylalanine, valine or leucine. As catalyst for an asymmetric hydrogenation in the heterogeneous phase, there can also be used a heavy metal catalyst which is applied to a natural or synthetic polymer, for example, palladium or platinum on silk or on a specially prepared silica gel or polyamino acid carrier, such as are described in the literature. In homogeneous phase, asymmetric hydrogenation can take place, for example, with the use of a soluble rhodium complex. The asymmetric hydrogenation is carried out under the abovegiven conditions, preferably at 1–3 atms. pressure and at a temperature of from about 20° to 50° C.

The compounds of general Formula I can also be obtained from compounds of general Formula IV by hydroxylation, hydroxlkylation, halogenation or nitration or by treatment with an agent giving off sulfur.

Hydroxylation of compounds of general Formula IV can take place, for example, in the 1-position by treating the starting material with hydrogen peroxide or with a derivative thereof, such as performic acid, peracetic acid, perbenzoci acid or 3-chloroperbenzoic acid. It is preferable to hydrogenate in an inert solvent, especially in methylene chloride, chloroform or diethyl ether, at a temperature of from 0° to 50° C. and more preferably from 20° to 30° C. The reaction is finished under these conditions after about 1 to 48 hours. It proceess especially well with starting materialls of general Formula IV in which $R^{13}$ is pyridyl-carbonyl.

A hydroxyalkyl group can be introduced into the 3-position of compounds of general Formula IV by hydroxyalkylation. Preferred as hydroxyalkylation agent is alkylene oxide or a haloalcohol of up to 4 carbon atoms, for example, ethylene oxide or 2-bromoethanol. The hydroxalkylation is, as a rule, carried out in an inert solvent, preferably in liquid ammonia and/or an ether, such as diethyl ether, tetrahydrofuran or dioxane, a strong base preferably being added as catalyst, especially sodamide, potassamide or lithamide, lithium diisopropylamide or butyl lithium. The reaction temperature is from about −80° to +30° C. The reaction is complete in about 1 to 48 hours.

It is also possible by halogenation to introduce one or more halogen atoms, preferably chloride or bromine atoms, into compounds of general Formula IV. Thus, compounds (IV) can be reacted with elemental chlorine or bromine in an inert solvent, such as diethyl ether, carbon tetrachloride or acetic acid, using, as catalysts, for example, iron filings, iodine, ferric chloride or aluminum chloride. The reaction temperatures are preferably from about −30° to +100° C. According to the methods described in the literature, the conditions can be so selected that the halogenation takes place preferentially in the aromatic nucleus or in the 7-position. In the aromatic nucleus, the 8- and 11-positions are preferably substituted. It is also possible that several halogenation products are formed simultaneously, which can be separated, for example, by chromatograhy or by crystallization. Halogenation is also possible with other halogenating reagents, for example, with acyl hypohalides or N-halo-imides, such as N-chloro o N-bromosuccinimide, in which case, as a rule, the reaction is carried out in an inert solvent in the given temperature range.

By treatment with nitrating agents, one or more nitro groups can be introduced into the molecule of the starting compounds of general Formula IV. Substitution preferably takes place in the 8- or 11-position. Preferred as nitrating agent is nitric accid or a derivative thereof, for example, a salt, ester, halide or anhydride (i.e., a nitrogen oxide). The nitration is advantageously carried out in the presence of an acidic catalyst, for example, sulfuric acid, as well as hydrofluoric acid or a Friedel-Crafts catalyst, such as boron trifluoride, aluminum trichloride or ferric chloride. An excess of the nitrating agent, for example, of nitric acid and/or an excess of the catalyst, for example, sulfuric acid, can simultaneously serve as solvent. However, it is also possible to carry out the nitration in the presence of one or more additional inert solvents. Acetic acid is preferred. It can also be advantageous to operate in a twophase system by using a chlorinated hydrocarbon, such as methylene chloride, chloroform or carbon tetrachloride as solvent. As a rule, the nitration is carried out at a temperature of from −20° to +50° C. and preferably of from 0° to 20° C.

By treatment of compounds of general Formula IV with an agent giving off sulfur, preferably with phosphorus pentasulfide, the carbonyl groups can be converted into thiocarbonyl groups. This reaction is preferably carried out in the presence of an inert solvent, such as tetrahydrofuran, dioxane, chloroform, carbon disulfide, benzene, toluene or a xylene, at a temperature of from about 20° to about 140° C. and is complete after about 1 to 12, usually about 2 to 6 hours.

Compounds of general Formula I in which $R^2$ is $CSR^9$ can be obtained by treating a compound of general Formula IV, wherein $R^{13}$ is a hydrogen atom, with a thioacylating agent. As thioacylating agent, there can be used, for example, compounds of the general formula $R^9$—CS—$E^1$ wherein $E^1$ is a hydroxyl group or O-alkyl, S-alkyl, S—$CH_2COOH$, $NH_2$, NH-alkyl or N(alkyl)$_2$ in which alkyl preferably is of up to 4 carbon atoms. Of these thioacylating agents, those of general formulae $R^9$—CS—S—$CH_2COOH$ and $R^9$—CS—$NH_2$ are preferred. The reaction can take place either in the absence of solvent, for example, by heating the reaction components, or in the presence of one or more inert solvents. As inert solvents, there can be used, for example, water, alcohols, such as methanol or ethanol, chlorinated hydrocarbons, such as chloroform, or hydrocarbons, such as benzene or toluene. The addition of a base, such as sodium hydroxide, potassium hydroxide, sodium carbonate, potassium carbonate, triethylamine or pyridine, is, as a rule, advantageous. The thioacylation is normally carried out at a temperature of from about 0° to about 150° C., the higher temperature range being preferred for the reaction with thioamides, for example, those of the general formula $R^9$—CS—$NH_2$. It can also be advantageous to operate under reduced pressure. As a rule, the reaction is complete after about 1 to 24 hours, usually about 6 to 12 hours.

Compounds of general Formula I wherein $R^2$ is —CO—$R^{11}$ can be obtained by reacting a compound of general Formula IV ($R^{13}$ = H) with a compound of general formula $R^{11}$—CO—E. Of these compounds, chloroformic acid esters of the general formula $R^{11}$—CO—Cl are preferred. As a rule, the reaction takes place in the presence of an inert solvent, for example, of a chlorinated hydrocarbon, such as dichloromethane, a basic catalyst, for example, pyridine or triethylamine, preferably being present. The reaction temperature is from about 0° to about 100° C., preferably from 20° to 60° C.

Some of the starting compounds of general formulae II, III and IV are known. Those that are not known can be prepared according to known methods.

For example, isoquinoline derivatives of general Formula IIa can be obtained by hydrogenating an appropriately substituted 1-cyano-1,2-dihydro- or 1-cyano-1,2,3,4-tetrahydro-2-$R^2$-isoquinolines in the presence of Raney nickel at an elevated temperature and pressure, with migration of the $R^2$ substituent, to give the corresponding 1-$R^2$-aminomethyl-1,2,3,4-tetrahydroisoquinolines, which can subsequently be converted with acid chlorides of the general formula E—CHR$^3$—CX—Cl into compounds of general Formula IIa. If, for example, chloroacetyl chloride is used in the last-mentioned stage, then compounds are obtained of general Formula IIa (X = O; $R^3$ = H, E = Cl).

Compounds of general Formula IIb can be obtained, for example, by the reaction of appropriate 1-aminomethyl-1,2,3,4-tetrahydroisoquinolines with glyoxalic acid and hydrogenation of the Schiff's bases obtained to give the corresponding 1-carboxymethylaminomethyl-1,2,3,4-tetrahydroisoquinolines (IIb) ($R^1 = R^2 = R^3 = H$; X = O; E = OH). By conversion of their carboxyl group, other compounds of general Formula IIb can be obtained in which the substituent E has a different value. Compounds of general Formula IIb in which $R^2$ is a hydrogen atom can also be obtained, for example, by hydrolysis of appropriate 2-Acyl compounds, for example, of 2-benzoyl-4-oxo-1,2,3,6,7,11b-hexahydro-4H-pyrazino[2,1-a]isoquinolines. In the course of this hydrolysis, the acetyl and benzoyl group in the 2-position can be simultaneously split off and the lactam ring opened. Furthermore, compounds of general Formula IIb can be obtained by various variants of the Pictet-Spengler synthesis. Thus, for example, appropriately substituted 2-phenylethylamines can be reacted with derivatives of 2-aminoacetaldehyde, for example, with compounds of the general Formula E—CX—CHR$^3$—NR$^2$—CHR$^1$—CH(O-alkyl)$_2$, in which the alkyl groups preferably contain up to 4 carbon atoms.

The starting materials of general Formula IIc can be prepared, for example, by condensing appropriately substituted phenyl-glyoxals with aminomalonic acid diamide to obtain 2-aminocarbonyl-3-hydroxy-5-phenylpyrazines. These can be converted by hydrolysis and decarboxylation into 3-hydroxy-5-phenyl-pyrazines from which, by hydrogenation, there are obtained 3-oxo-5-phenyl-piperazines. The reaction thereof with compounds of the general formula $R^2$—Cl and compounds of the general formula E—CHR$^4$—CR$^5$—E (wherein the two E groups are preferably different, for example, chloroacetic acid and its derivatives) or equivalents thereof (for example, alkylene oxides) produces the desired compounds of general Formula IIc.

Starting materials of general Formula III which contain a double bond in the 11b(1)-position, can be obtained, for example, by the Bischler-Napieralski synthesis from appropriately substituted 1-(2-phenylethyl)-4-$R^2$-2,6-piperazine-diones. Compounds of general Formula III with a double bond in the 6(7)-position can be obtained, for example, from the appropriate 7-oxo compounds by reduction and subsequent dehydration. The compounds of general Formula III in which $R^{12}$ is an alkylidene group can be obtained from the same 7-oxo compounds and triphenyl phosphine alkylenes.

Starting materials of general Formula III which contain a double bond in the 11b(1)-position can be obtained by dehydrogenation of the corresponding saturated compounds with sulfur, selenium, chloranil or other dehydrogenation agents. The preparation of these starting materials is especially of interest when compounds saturated in the 11b(1)-position (which are within the scope of compounds of general Formula I), are present as optically-active antipodes and are less effective than one of the other possible antipodes. In this case, the less active antipode can be converted by dehydrogenation into a compound (III) and, by subsequent hydrogenation, converted into the more active saturated racemate of general Formula I or, by asymmetric hydrogenation, substantially converted into the more active antipodes of general Formula I.

The starting materials of general Formula IV in which $R^{13}$ is a hydrogen atom or benzoyl, are known. The other compounds of general Formula IV can be obtained, for example, by acylation of the corresponding compounds which are unsubstituted in the 2-position.

In a thus-obtained compound of general Formula I, one or more of the $R^1$ to $R^8$ and X groups can be converted into a corresponding group having another value.

More specifically, it is possible, in a thus-obtained compound of general Formula I, by treatment with a hydroxylating agent to introduce a hydroxy group, with a hydroxyalkylating agent to introduce a hydroxyalkyl radical, with a halogenating agent to introduce one or more halogen atoms and/or with a nitrating agent to introduce one or more nitro groups and/or by treatment with an agent giving off sulfur, to convert one or more oxo groups into thioxo groups and/or to convert a compound of general Formula I in which $R^2$ is a hydrogen atom, with a thioacylating agent into the corresponding thioamide (I) ($R^2$ = CS—$R^9$) or, by reaction with a compound of the formula $R^{11}$—CO—E, into the corresponding carbonic acid derivative (I) ($R^2$ = CO—$R^{11}$). The abovedescribed methods are thereby employed but, instead of using a compound of general Formula IV, there is used as starting material an appropriately substituted product of general Formula I.

In a thus-obtained compound of general Formula I, groups which can be split off by solvolysis, especially acyl radicals, can be split off by treatment with a solvolyzing agent and/or amino and/or hydroxyl groups can be acylated by treatment with an acylating agent and/or alkylated by treatment with an alkylating agent and/or reducible groups present, especially keto, hydroxyl and/or nitro groups and/or halogen atoms, can be reduced by treatment with a reducing agent or can be replaced by hydrogen and/or carbon-carbon double bonds present can be hydrogenated and/or amino groups present can be diazotized by treatment with nitrous acid or with a derivative thereof and the diazonium group of the compounds obtained subsequently replaced by a halogen atom or by a hydroxy, alkoxy, cyano or Z group and/or a hydroxy group converted by treatment with an inorganic acid halide into a halogen atom and/or a keto group converted by treatment with a fluorination agent into a CF$_2$ group or by reductive amination converted into an amino group.

Solvolytic splitting off of acyl radicals or of thioacyl radicals in the 2-position and/or of acyl radicals from the $R^6$ or $R^7$ groups (when they are acyloxy, acylamino or benzoyloxy), preferably takes place by treatment with a solvolyzing agent in an acidic or alkaline medium. The conditions must thereby be so selected that the lactam group is not simultaneously split off. Therefore, mild reaction conditions are preferred. As acids, there can be used for the solvolysis, for example, mineral acids, such as phosphoric acid, sulfuric acid or hydrochloric acid, as well as acid salts, such as potassium hydrogen sulfate. As bases, there can be used, for example, alkali metal or alkaline earth metal hydroxides, such as sodium, potassium, calcium or barium hydroxide, alkali metal carbonates, such as sodium or potassium carbonate, alkali metal alcoholates, such as sodium or potassium methylate or ethylate, as well as, for example, hydrazine hydrate. As a rule, the solvolysis is carried out in an aqueous, aqueous-alcoholic or alcoholic medium, for example, in methanol or ethanol. However, it is also possible to employ an excess of the acid, for example of sulfuric or phosphoric acid, in which case water can also be present. Methanolic or ethanolic hydrochloric acid can also be used as solvolyzing agent. The reaction temperatures for the solvolysis are from about −50° to +200° C. and preferably from about 20° to 150° C. The solvolysis is complete after about 0.5 to 72 hours, usually about 2 to 48 hours.

A solvolytic splitting of alkoxy radicals, especially of aromatically-bound alkoxy radicals, in the compounds obtained of general Formula I can be carried out with, for example, Lewis acids, such as boron tribromide, in inert solvents, such as methylene chloride or chloroform, at temperatures of from about −40° to +50° C.

Acylation of amino and/or hydroxy groups in a compound obtained of general Formula I can be carried out with appropriate carboxylic acids or functional derivatives thereof. For the acylation of an amino group in the 2-position, there can be used carboxylic acids of the general formula $R^9$—COOH. For the acylation of hydroxy and/or amino groups which are in the aromatic nucleus, there can, on the other hand, be used fatty acids of up to 4 carbon atoms. Benzoic acid can also be used for O-acylation. As functional derivatives, there are preferably used the carboxylic acid anhydrides, for example, acetic anhydride, as well as mixed carboxylic acid anhydrides, for example p-fluorobenzoic acid-formic acid anhydride, carboxylic acid halides, preferably the chlorides and bromides, such as acetyl chloride or bromide, and also the corresponding azides or esters, especially the alkyl esters in which alkyl preferably is of up to 4 carbon atoms. When carrying out the acylation, an inorganic or organic base is advantageously added, for example, an alkali metal hydroxide or carbonate, such as sodium or potassium hydroxide or sodium or potassium carbonate, or a tertiary amine, such as triethylamine, triisopropylamine or pyridine. As a rule, the reaction is carried out in the presence of an inert solvent, for example, of an ether, such as diisopropyl ether, tetrahydrofuran or dioxane, of a halogenated hydrocarbon, such as dichloromethane, chloroform, carbon tetrachloride or chlorobenzene, or of a hydrocarbon, such as benzene or toluene. However, as solvent there can also be used an excess of the carboxylic acid derivative and/or an excess of the added base. Furthermore, it is possible to produce the actual acylating agent in situ. For example, the carboxylic acid halides can be produced in situ from the carboxylic acids with the use of halogenating agents, for example, tin tetrachloride, phosphorus trichloride, phosphorus tribromide, phosphorus oxychlride, thionyl chloride or phosphorus pentachloride, the reaction thereby being carried out in the presence or absence of the above-mentioned bases and/or solvents. In carrying out the acylation, an agent splitting off water can also be added. For example, acylation can be carried out with the free carboxylic acid in the presence of a carbodiimide, such as dicyclohexyl carbodiimide, in one of the above-mentioned solvents. The reaction temperatures for the acylation can be between about 0° and about 200° C. and preferably between about 20° and 80° C. The reaction is complete after about 10 minutes to 72 hours and usually about 1 to 24 hours.

Acylation can also be carried out with ketenes, preferably in one of the above-mentioned solvents, with the addition of an acidic catalyst, such as p-toluene-sulfonic acid or sulfuric acid.

Compounds of general Formula I which contain one or more free hydroxy, amino or monoalkylamino groups as substituents can be aklyated to give the corresponding alkoxy, monoalkylamino or dialkylamino compounds or to give the corresponding trialkyl ammonium salts.

The alkylation can be carried out according to conventional methods by treatment with an alkylating agent. For O-alkylation, the starting materials are preferably first converted into corresponding salts (phenolates) by the addition of a base, for example of sodium hydroxide, potassium hydroxide or potassium carbonate. As alkylation agents, there can be used, for example, alkyl halides, such as methyl chloride, bromide or iodide, ethyl chloride, bromide or iodide or the corresponding dialkyl sulfuric acid or alkyl sulfonic acid esters, for example dimethyl sulfate, diethyl sulfate or methyl p-toluene-sulfonate. Diazo compounds, such as diazomethane, can also be used for the O-alkylation. Amino compounds can be alkylated with these reagents but also reductively with aldehydes, such as formaldehyde or acetaldehyde, for example in the presence of hydrogen or formic acid. If the reaction is carried out in the presence of hydrogen, then it is expedient to add one of the catalysts mentioned above for the reduction of compounds of general Formula III. As solvent, there can be used, for example, waer or aqeuous sodium hydroxide solution, an alcohol, such as methanol, ethanol or n-butanol, an ether, such as tetrahydrofuran or dioxane, an amide, such as dimethylformamide, or a hydrocarbon, such as benzene or a xylene. Solvent mixtures can also be employed. The addition of a base, for example of an alkali metal hydroxide, such as sodium or potassium hydroxide, or of a tertiary amine, such as pyridine or triethylamine, can also be useful.

In the case of the N-alkylation, depending upon the choice of the reaction conditions and of the amount of the added alkylation agent, there can be preponderantly obtained mono- or dialkylamino compounds or trialkyl ammonium salts. The reaction temperature for the alkylation is preferably from about −10° to about 150° C. and more preferably from about 20° to 100° C.

Furthermore, reducible groups and/or carbon-carbon double bonds present in the compounds obtained of general Formula I can be reduced by treatment with a reducing agent or can be replaced by hydrogen. Reducible groups are, in particular, keto and/or hydroxyl groups in the 7-position, nitro groups in the 8-, 9-, 10- or 11-position or as a component of $R^9$, for example as a substituent on a cycloalkyl, cycloalkenyl or phenyl group, halogen atoms in the 7-, 8-, 9-, 10- or 11-position or as a component of $R^9$, for example, as a substituent on a cycloalkyl, cycloalkenyl or phenyl radical. Reducible carbon-carbon double bonds can occur especially in the radical $R^9$ if this is, for example, a cycloalkenyl group.

These groups and especially carbon-carbon double bonds can be reduced according to the above-described methods of catalytic hydrogenation.

Besides the catalytic hydrogenation, other methods of reduction can also be employed. However, care must thereby be taken that the lactam or thiolactum group of the ring system is not attacked. However, according to the statements in the literature, this is easily possible. Thus, for the reduction of, for example, keto or nitro groups, reaction with nascent hydrogen can be used, which can be produced, for example, by the treatment of metals with acids or bases. Thus, for example, there can be used the systems zinc/acid, iron/acid, tin/acid, or zinc/aqueous alkali metal hydroxide solution. As acids, there can be used, for exaple, hydrochloric acid or acetic acid. Furthermore, as reducing agents, there can be employed alkali metals, for example sodium, in an alcohol, such as ethanol, isopropanol or isoamyl alochol; complex metal hydrides, which do not attack the lactam group, such as sodium borohydride, lithium borohydride or potassium trimethoxyborohydride; stannous chloride; or hydrazine. The reduction can be carried out in the presence of an additional inert solvent, those solvents being employed which are known from the literature for the individual reduction methods. Thus, for example, complex metal hydrides are used in an ether, such as diethyl ether, tetrahydrofuran, dioxane, 1,2-dimethoxyethane or diglyme, and sodium borohydride also in alcoholic solution, for example, in methanolic or ethanolic solution, or in aqueous alcoholic or aqueous solution. In general, the reduction reaction is carried out at a temperature of from about $-80°$ to $+250°$ C. and preferably of from $-20°$ to $+100°$ C.

Keto groups and especially keto groups in the 7-position can be converted into methylene groups by catalytic hydrogenation on palladium catalysts or by reaction with hydrazine and subsequent thermal decomposition of the hydrazone formed, by the Wolff-Kishner method. The last-mentioned reaction is preferably carried out in the presence of a strong base and of a high boiling solvent, such as diethylene glycol.

In a compound obtained of general Formula I which contains one or more aromatically bound amino groups, these groups can be converted by diazotization into the corresponding diazonium compounds. Diazotization can be carried out, for example, in acidic aqueous solution, for example in the presence of sulfuric acid, hydrochloric acid, hydrobromic acid or tetrafluoroboric acid, by the addition of an inorganic nitrite, preferably of sodium or potassium nitrite, at a temperature of from about $-20°$ to $+10°$ C. It is also possible to use an organic nitrite, for example, n-butyl nitrite, n-amyl nitrite or isoamyl nitrite, at a temperature of from about $-20°$ to $+10°$ C. in an inert solvent, such as diethyl ether, tetrahydrofuran or dioxane.

The diazonium group in the diazonium compounds thus obtained can be exchanged, for example, for fluorine, chlorine, bromine, iodine, hydroxyl, alkoxy, cyano or Z groups.

For the introduction of a fluorine atom, diazotization is carried out, for example, with anhydrous hydrofluoric acid and then subsequently heated or the diazonium salt is reacted with tetrafluoroboric acid to give the sparingly-soluble diazonium tetrafluoroborates. These can be isolated and thermally converted into the desired fluoro compounds, for example by heating in an inert solvent. The diazonium tetrafluoroborates can also, without isolation, be decomposed in aqueous suspension by irradiation with a mercury lamp. The diazonium group can be exchanged for chlorine or bromine, preferably in hot solution, in the presence of cuprous chloride or cuprous bromide, by Sandmeyer's method. The exchange of a diazonium iodide group for iodine even takes place by slight heating, whereby there can also be added catalysts, such as cuprous iodide, bromide or chloride. Hydrolysis of the diazonium salts, preferably with heating, leads to the corresponding hydroxy compounds. The diazonium salt grouping can also be exchanged for an alkoxy radical, for example, by heating in an aqeuous-alcoholic solution. The replacement of the diazonium group for a cyano group can be carried out, for example, by Sandmeyer's method in the presence of cuprous cyanide and an alkali metal cyanide, such as sodium or potassium cyanide, even in the cold, for example, at a temperature of from about 0° to $+50°$ C.

The diazonium compounds can also be coupled with approprite coupling components to give azo dyestuffs of the general Formula I, in which $R^6$ or $R^7$ are Z and/or $R^9$ is a Z-substituted phenyl radical. These compounds have, compared to the basic amino compounds, the advantage of being more stable and of being easier to incorporate into pharmaceutical formulations. As coupling components, most preferred are benzene and naphthalene derivatives which can easily be coupled, for example, those which carry in the p-position activating substituents, such as amino, alkylamino, dialkylamino, hydroxy or alkoxy groups, and, in addition, can also contain further substituents, such as carboxy, halogen, preferably fluorine or chlorine, sulfo or alkyl.

It is also possible to convert a hydroxy group present in the product obtained of general Formula I, especially an aliphatically-bound hydroxy group, by treatment with an inorganic acid halide, such as thionyl chloride, phosphorus trichloride, phosphorus tribromide, or phosphorus pentachloride, into a halogen atom. It is preferable to work in the presence of an inert solvent, such as dichloromethane, chloroform or carbon tetrachloride, at a temperature of from about 20° to about 80° C.

It is also possible to convert a keto group in $R^9$ into a $CF_2$ group, for example, with sulfur tetrafluoride or phenyl sulfur trifluoride, in the presence of hydrogen fluoride or also with carbonyl difluoride in the presence of pyridine. In these reactions, it is preferable to employ inert solvents, such as methylene chloride, chloroform or tetrahydrofuran. The reaction temperature can be from about 0° to 150° C. and is preferably from about 20° to 50° C. It can also be advantageous to operate under pressure.

When a keto group is present in $R^9$, it can be converted by reductive amination in one or more stages into an amino group. Thus, for example, it is possible to convert a keto group with hydroxylamine into an oxime or with hydrazine into a hydrazone and catalytically to hydrogenate the derivatives thus-obtained, for example, on Raney nickel, at 1 to 50 and preferably at about 5 to 10 atms. pressure. It is also possible to hydrogenate the ketone in the presence of ammonia or of a monoalkylamine or dialkylamine, preferably at a pressure of from about 1 to 200 and especially of from 80 to 120 atms. pressure. As solvents for the last-mentioned form of amination, there can be used, for example, alcohols, such as methanol, ethanol or isopropanol, as well as ethers, such as tetrahydrofuran or dioxane. Liquid ammonia can also be employed. The reaction temperatures can be from about $-40°$ to $+150°$ C., preferably about 60° to 80° C. The reaction times are about 4 to 24 hours, preferably about 8 to 12 hours.

A free base of general Formula I can be converted in a conventional manner with an acid into an acid addition salt thereof. For this reaction, those acids can be used which give physiologically acceptable salts. Thus, inorganic acids can be used, for example, sulfuric acid, nitric acid, hydrohalic acids, such as hydrochloric acid, hydrobromic acid or hydriodic acid, phosphoric acids, such as orthophosphoric acid, or sulfamic acid; and organic acids, especially aliphatic, alicyclic, araliphatic, aromatic or heterocyclic mono- or polybasic carboxylic or sulfonic acids, such as formic acid, acetic acid, propionic acid, butyric acid, pivalic acid, diethylacetic acid, oxalic acid, malonic acid, succinic acid, pimelic acid, fumaric acid, maleic acid, lactic acid, tartaric acid, malic acid, gluconic acid, citric acid, benzoic acid, salicylic acid, phenylpropionic acid, ascorbic acid, nicotinic acid, isonicotinic acid, methane- and ethane-sulfonic acid, ethane-disulfonic acid, 2-hydroxyethane-sulfonic acid, benzene-sulfonic acid, p-toluene-sulfonic acid, naphthalene-mono- or disulfonic acids, for example naphthalene1- or -2-sulfonic acid or naphthalene-1,5- or -2,6-disulfonic acid, can be used.

Acidic compounds of general Formula I and especially those which contain a phenolic hydroxyl group and/or a carboxyl group and/or a sulfo group, can, by treatment with a base, be converted into the corresponding physiologically compatible metallic or ammonium salts. Preferred salts include the sodium, potassium, calcium, ammonium and substituted ammonium salts, for example, the cyclohexyl, benzyl or triethanol ammonium salts.

Compounds of general Formula I which carry a primary, secondary or tertiary amino group, can, by treatment with a quaternizing alkylation agent, such as a methyl or ethyl halide or dimethyl sulfate, and preferably with an excess of such an alkylation agent, be converted into their physiologically compatible quaternary ammonium salts.

The free bases of general Formula I can, if desired, be liberated from their salts by tratment with strong bases, such as sodium or potassium hydroxide or sodium or potassium carbonate. Analogously, the acidic compounds of general Formula I can be liberated from their metallic or ammonium salts by treatment with a strong acid, such as hydrochloric acid or sulfuric acid.

In some of the above-described reactions, products are obtained of indefinite constitution. For example by halogenation or nitration of compounds of general Formula IV or of compounds of general Formula I, wherein $R^6$ and $R^7$ are hydrogen atoms, products are formed in which the position of the newly introduced substituents is not known. The position of the substituents is, in the case of such compounds, indicated in the following with a question mark or an alternative statement, i.e., "-8(?)-bromo" means, for example, that in the product in question, the bromine atom is presumably but not proven to be in the 8-position. Similarly, "8-(or 11)-nitro," for example, means that in the compound in question, the nitro group is, in all probability, in the 8- or 11-position but that the exact position of the nitro group has not definitely been established.

The compounds of general Formula I possess at least one center of asymmetry in the 11b-position. In the case of appropriate substitution, they can possess further centers of asymmetry. Therefore, in the case of their syntheses, they can be obtained as racemates or, if optically-active starting materials have been used, can also be obtained in optically-active form. If the compounds have two or more centers of asymmetry, then they are generally obtained from the syntheses in the form of mixtures of racemates from which the individual racemates can be isolated in pure form, for example by recrystallization or by chromatography. However, it is also possible that only one of the possible racemates is preponderantly or exclusively obtained. This is especially the case when starting from a sterically uniform starting material. In this connection, those compounds of general Formula I are to be particularly mentioned in which $R^4$ is other than hydrogen, i.e., alkyl or phenyl and especially methyl. These compounds are, in the following, called cis compounds when the hydrogen atom in the 6- and 11b-position is in the cis position, for example, 6-cis-methyl. Otherwise, they are called trans compounds. The stereochemical assignment has taken place with great probability but not with absolute certainty.

Racemates obtained can, if desired, be mechanically or chemically separated into their optical antipodes by known methods. From the racemates there are preferably formed diastereomers by reaction with optically-active separating agents. For example, a racemate of general Formula I which contains a basic group, for example, an amino group, can be converted with an optically-active acid into the corresponding salt. As acids for this purpose, there can be used, for example, dextro- and laevo-rotary antipodes of tartaric acid, dibenzoyltartaric acid, diacetyltartaric acid, camphoric acid, camphor-sulfonic acids, mandelic acid, malic acid, lactic acid, 2-phenylbutyric acid, dinitrodiphenic acid or quinic acid. Racemates of general Formula I which contain an acidic group, for example a carboxylic acid or sulfonic group, can be reacted analogously with an optically-active base, for example, with strychnine, brucine, quinine or one of the optically-active forms of 1-phenylethylamine. The diastereomeric mixtures obtained can subsequently be separated by crystallization or by manual selection. The desired optically-active antipodes of the compounds of general Formula I can subsequently be obtained by hydrolytic decomposition of the isolated diastereomeric salts.

The compounds of general Formula I and their physiologically acceptable salts have an excellent activity against cestodes and trematodes. They can, for example, be used against the following cestodes (arranged according to host):

1. Ruminants: Moniezia, Stilesia, Avitellina, Thysanosoma, Thysaniezia, hydatids of *Taneia sp.*, *Coenurus cerebralis, Echinococci hydatids;*
2. Ungulates: Anoplocephala;
3. Rodents: Hymenolepis (especially *H. nana* and *H.diminuta*);
4. Birds: Davainea, Raillietina, Hymenolepis;
5. Canines and felines: Taenia (especially *T. hydatigena, T. pisiformis, T. taeniaeformis, T. ovis, T. serialis, T. cervi, T. multiceps*), Dipylidium (especially *D. caninum*), Echinococcus (especially *E. granulosus* and *E. multilocularis*);
6. Humans: Taenia (especially *T. solium, T, saginata, T. serialis*), Hymenolepis (especially *H. nana* and *H. diminuta*), Drepanidotaenia, Dipylidium, Diplopylidium, Coenurus (especially *C. cerebralis,* Diphyllobothrium (especially *D. latum*), Echinococcus hydatids (especially *E. granulosis* and *E. multilocularis*).

The trematodes which are important to combat in human and veterinary medicine include those of the families Schistosomidae, especially of the genus Schistosoma (*Sch. mansoni, Sch. haemotobium* and *Sch. japonicum*). The genuses Fasciola, Dicrocoelium, Clonorchis, Opisthorchis, Paragonimus, Paramphistomum, Echinostoma and the like can possible also be influenced.

The compounds of general Formula I and their physiologically acceptable salts can be used, inter alia, in the following host and/or intermediate host organisms for combating cestodes or trematodes and/or their larvae: humans, various species of monkeys, as well as the most important domestic and wild animals, for example, the various canines, such as dogs and foxes; felines, such as cats; ungulates, such as horses, donkeys and mules; cervids, such as roe, red and fallow deer, chamois; rodents; ruminants, such as cows, sheep and goats; birds, such as hens and ducks; pigs; fish and the like.

Habitats of susceptible parasites or of their larvae include, in particular, the gastro-intestinal tract, for example, the stomach, intestines, pancreas and bile duct. However, various other organs include, for example, liver, kidneys, heart, spleen, lymph nodes, brain, spinal cord and testes, the abdominal cavity, connective tissue, musculature, peritoneum, pleura, diaphragm, lungs, and blood vessels; thus, the compounds of general Formula I are active, with good compatibility, for example, against *Schistosoma sp.* in the blood vessels, against *Hymenolepis microstoma* in the bile duct and against *T. hydatigena* hydatids in the liver.

The compounds of general Formula I and their physiologically acceptable salts can be used as such or in combination with pharmaceutically acceptable, inert carriers. Carriers of this type can include, for example, capsules, solid diluents or filler materials, sterile aqeuous media and/or various non-toxic organic solvents.

Forms of administration which can be used include, for example, tablets and dragees (which can also contain the active material in depot form), effervescent tablets, capsules, granulates, aqueous suspensions, injectable solutions, emulsions and suspensions, elixirs, syrups or pastes. The formulations for this purpose can be prepared in known manner, for example, by the addition of the active materials to solvents and/or carrier materials, optionally with the use of emulsifying agents and/or dispersion agents. As adjuvants, there can be used, for example, water, non-toxic organic solvents (e.g., paraffins or alcohols, such as glycerol or polyethylene glycol), vegetable oils (e.g., sesame oil), solid carrier materials, such as natural or synthetic mineral powders (e.g., talc or highly dispersed silicic acid), sugars, emulsifiers (e.g., ionic or non-ionic), dispersion agents (e.g., methyl-cellulose of polyvinyl-pyrrolidone) and/or lubricants (e.g., magnesium stearate). Tablets can also contain additives, such as sweetening agents, sodium citrate, calcium carbonate and dicalcium phosphate, together with other additives, such as starch, gelatine and the like. Aqueous suspensions and/or elixirs can, if desired, contain flavor improvers and/or coloring materials. The active compounds can, if desired, also be administered without or almost without adjuvants, for example in capsules.

The active compounds are preferably administered orally but parenteral, especially subcutaneous or intramuscular, as well as dermal administration is also possible.

For combatting adult cestodes, it is advantageous to administer the active materials one or more times daily in amounts of from 0.01 to 250 mg/kg. and preferably of from about 0.5 to 100 mg/kg., orally or subcutaneously. For combatting the corresponding tapeworm larvae (hydatids) or Schistosoma, larger amounts of active material may be necessary.

When administering comparatively large amounts of active material, they can also be divided over the course of the day into smaller individual dosages. Thus, instead of a single 1000 mg. dose, five separate dosages, each of 200 mg., can be administered. In veterinary medicine, administration with the animal feed can also be used, in which case it is preferable first to prepare an appropriate pre-mix containing the active material. Here again, all conventional additive materials can also be used.

If necessary, it is possible to deviate from the abovementioned amounts, depending upon the body weight or the nature of the route of application but also on the basis of species and of the individual behavior thereof towards the medicament or the nature of its formulation or the point of time or interval at which administration takes place. Thus, in some cases, it can suffice to administer less than the abovementioned minimum amount, whereas, in other cases, it is necessary to exceed the upper limit.

Depending upon the nature of the administration, the ratio between the active compounds and the carrier and/or adjuvant employed can vary very considerably. If, for example, an active compound is administered as a tablet or dragee, then about 0.01 to 2500 mg. of active material can be combined with about 1 to 10,000 mg. of adjuvant. If, on the other hand, an active compound is formulated as a premix for a medicated feed, then for each 1 kg. of carrier or adjuvant material, there can be used about 0.1 to 400 g. of active compound. When formulated as an injection liquid, a solution of 1 liter of liquid can contain, depending upon the nature of the solubilizing agent, about 0.5 to 100 g. of active compound. Similarly, 1 liter of syrup can contain dissolved or suspended therein about 0.5 to 250 g. of active compound.

The active compounds can also be present in the formulations in admixture with other active materials. Thus, to achieve a broader spectrum of activity, it is sometimes useful to add a material active against nematodes, for example, thiabendazole [2-(4-thiazolyl)-benzimidazole] or piperazine (or piperazine derivatives, such as N-methylpiperazine). It is also possible to administer a mixture of two or more compounds of general Formula I and/or their physiologically acceptable salts.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the following examples, the "usual working up" means the following procedure: if necessary, there is added water and/or organic extraction agent, such as dichloromethane, chloroform or an ether, followed by separation, washing the organic phase with dilute hydrochloric acid (provided that the product is not basic) and with water, separation, drying over anhydrous magnesium or sodium sulfate, evaporation and purification of the crude product by crystallization and/or chromatography. The infra-red spectra are measured in potassium bromide. The abbreviation "HPI" employed in the following examples means "1,2,3,6,7,11b-hexahydro-4H-pyrazino[2,1-a]isoquinoline."

EXAMPLE 1 a. 300 ml. of a 20% n-butyl lithium solution in hexane are added, under an atmosphere of nitrogen, at 5° – 10° C. and with vigorous stirring to b 216 g. N-(2-chloroacetyl-3-cis-methyl-1,2,3,4-tetrahydroisoquinolyl-1-methyl)-benzamide (m.p. 140° C.; obtainable from N-(3-cis-methyl-1,2,3,4-tetrahydroisoquinolyl-1-methyl)-benzamide by reaction with chloroacetyl chloride) in 4 liters anhydrous tetrahydrofuran. The reaction mixture is stirred for 2 hours at 20° C., then hydrolyzed with water, whereafter the solvent is evaporated off and the residue worked up as usual to give 2-benzoyl-4-oxo-6-cis-methyl-HPI which, after recrystallization from methanol, melts at 165° C.

The following compounds are obtained in an analogous manner by cyclizing the appropriate isoquinoline derivatives:

2-acetyl-4-oxo-6-cis-methyl-HPI
2-propionyl-4-oxo-6-cis-methyl-HPI
2-butyryl-4-oxo-6-cis-methyl-HPI
2-isobutyryl-4-oxo-6-cis-methyl-HPI; m.p. 136° C.
1-methyl-2-isobutyryl-4-oxo-HPI
2-isobutyryl-3-methyl-4-oxo-HPI
2-isobutyryl-4-oxo-6-cis-methyl-HPI
2-isobutyryl-4-oxo-6-trans-methyl-HPI
2-isobutyryl-4-oxo-7-methyl-HPI
2-isobutyryl-4-oxo-8-methyl-HPI
2-isobutyryl-4-oxo-9-methyl-HPI
2-isobutyryl-4-oxo-b 10-methyl-HPI
2-isobutyryl-4-oxo-11-methyl-HPI
2-isobutyryl-4-oxo-11b-methyl-HPI
2-valeryl-4-oxo-6-cis-methyl-HPI
2-trimethylacetyl-4-oxo-6-cis-methyl-HPI
2-capronyl-4-oxo-6-cis-methyl-HPI
2-oenanthoyl-4-oxo-6-cis-methyl-HPI
1-methyl-2-cyclohexylcarbonyl-4-oxo-HPI
1-n-butyl-2-cyclohexylcarbonyl-4-oxo-HPI
2-cyclohexylcarbonyl-3-methyl-4-oxo-HPI
2-cyclohexylcarbonyl-3-ethyl-4-oxo-HPI
2-cyclohexylcarbonyl-3-n-butyl-4-oxo-HPI
2-cyclohexylcarbonyl-4-oxo-6-cis-methyl-HPI
2-cyclohexylcarbonyl-4-oxo-6-trans-methyl-HPI; m.p. 134° C.
2-cyclohexylcarbonyl-4-oxo-5-cis-ethyl-HPI
2-cyclohexylcarbonyl-4-oxo-6-trans-ethyl-HPI
2-cyclohexylcarbonyl-4-oxo-6-cis-isopropyl-HPI
2-cyclohexylcarbonyl-4-oxo-6-trans-isopropyl-HPI
2-cyclohexylcarbonyl-4-oxo-6-cis-phenyl-HPI
2-cyclohexylcarbonyl-4-oxo-6-trans-phenyl-HPI
2-cyclohexylcarbonyl-4-oxo-7-methyl-HPI
2-cyclohexylcarbonyl-4-oxo-7-ethyl-HPI
2-cyclohexylcarbonyl-4-oxo-7-phenyl-HPI
2-cyclohexylcarbonyl-4-oxo-8-methyl-HPI
2-cyclohexylcarbonyl-4-oxo-8-ethyl-HPI
2-cyclohexylcarbonyl-4-oxo-9-methyl-HPI
2-cyclohexylcarbonyl-4-oxo-9-ethyl-HPI
2-cyclohexylcarbonyl-4-oxo-10-methyl-HPI
2-cyclohexylcarbonyl-4-oxo-10-ethyl-HPI
2-cyclohexylcarbonyl-4-oxo-11-methyl-HPI
2-cyclohexylcarbonyl-4-oxo-11-ethyl-HPI
2-cyclohexylcarbonyl-4-oxo-11b-methyl-HPI; m.p. 143° C.
2-cyclohexylcarbonyl-4-oxo-11b-ethyl-HPI
2-cyclohexylcarbonyl-4-oxo-11b-n-butyl-HPI
2-cyclohexylcarbonyl-4-oxo-9,10-dimethoxy-HPI
1-methyl-2-(4-oxo-cyclohexylcarbonyl)-4-oxo-HPI
2-(4-oxo-cyclohexylcarbonyl)-3-methyl-4-oxo-HPI
2-(4-oxo-cyclohexylcarbonyl)-4-oxo-6-cis-methyl-HPI
2-(4-oxo-cyclohexylcarbonyl)-4-oxo-6-trans-methyl-HPI; m.p.118° – 120° C.
2-(4-oxo-cyclohexylcarbonyl)-4-oxo-7-methyl-HPI
2-(4-oxo-cyclohexylcarbonyl)-4-oxo-8-methyl-HPI
2-(4-oxo-cyclohexylcarbonyl)-4-oxo-9-methyl-HPI
2-(4-oxo-cyclohexylcarbonyl)-4-oxo-10-methyl-HPI
2-(4-oxo-cyclohexylcarbonyl)-4-oxo-11-methyl-HPI
2-(4-oxo-cyclohexylcarbonyl)-4-oxo-11b-methyl-HPI
1-methyl-2-(tetrahydropyranyl-4-carbonyl)-4-oxo-HPI
2-(tetrahydropyranyl-4-carbonyl)-3-methyl-4-oxo-HPI
2-(tetrahydropyranyl-4-carbonyl)-4-oxo-6-cis-methyl-HPI; m.p. 156° – 159° C.
2-(tetrahydropyranyl-4-carbonyl)-4-oxo-6-trans-methyl-HPI
2-(tetrahydropyranyl-4-carbonyl)-4-oxo-7-methyl-HPI
2-(tetrahydropyranyl-4-carbonyl)-4-oxo-8-methyl-HPI
2-(tetrahydropyranyl-4-carbonyl)-4-oxo-9-methyl-HPI
2-(tetrahydropyranyl-4-carbonyl)-4-oxo-10-methyl-HPI
2-(tetrahydropyranyl-4-carbonyl)-4-oxo-11-methyl-HPI
2-(tetrahydropyranyl-4-carbonyl)-4-oxo-11b-methyl-HPI
1-methyl-2-(thiacyclohexyl-4-carbonyl)-4-oxo-HPI
2-(thiacyclohexyl-4-carbonyl)-3-methyl-4-oxo-HPI
2-(thiacyclohexyl-4-carbonyl)-4-oxo-6-cis-methyl-HPI
2-(thiacyclohexyl-4-carbonyl)-4-oxo-6-trans-methyl-HPI
2-(thiacyclohexyl-4-carbonyl)-4-oxo-7-methyl-HPI
2-(thiacyclohexyl-4-carbonyl)-4-oxo-8-methyl-HPI
2-(thiacyclohexyl-4-carbonyl)-4-oxo-9-methyl-HPI
2-(thiacyclohexyl-4-carbonyl)-4-oxo-10-methyl-HPI
2-(thiacyclohexyl-4-carbonyl)-4-oxo-11-methyl-HPI
2-(thiacyclohexyl-4-carbonyl)-4-oxo-11b-methyl-HPI
1-methyl-2-benzoyl-4-oxo-HPI
2-benzoyl-3-methyl-4-oxo-HPI; m.p. 176° C.
2-benzoyl-3-ethyl-4-oxo-HPI
2-benzoyl-3-n-propyl-4-oxo-HPI
2-benzoyl-3-isopropyl-4-oxo-HPI
2-benzoyl-3-n-butyl-4-oxo-HPI
2-benzoyl-4-oxo-6-trans-methyl-HPI; m.p. 195° C.
2-benzoyl-4-oxo-6-cis-ethyl-HPI
2-benzoyl-4-oxo-6-trans-ethyl-HPI
2-benzoyl-4-oxo-6-cis-n-propyl-HPI
2-benzoyl-4-oxo-6-trans-n-propyl-HPI
2-benzoyl-4-oxo-6-cis-isopropyl-HPI
2-benzoyl-4-oxo-6-trans-isopropyl-HPI
2-benzoyl-4-oxo-6-cis-n-butyl-HPI
2-benzoyl-4-oxo-6-trans-n-butyl-HPI
2-benzoyl-4-oxo-6-cis-isobutyl-HPI
2-benzoyl-4-oxo-6-trans-isobutyl-HPI
2-benzoyl-4-oxo-6-cis-sec.-butyl-HPI
2-benzoyl-4-oxo-6-trans-sec.-butyl-HPI
2-benzoyl-4-oxo-6-cis-tert.-butyl-HPI
2-benzoyl-4-oxo-6-trans-tert.-butyl-HPI
2-benzoyl-4-oxo-6-cis-phenyl-HPI
2-benzoyl-4-oxo-6-trans-phenyl-HPI
2-benzoyl-4-oxo-7-methyl-HPI; m.p. 157° C.
2-benzoyl-4-oxo-7-ethyl-HPI
2-benzoyl-4-oxo-7-n-propyl-HPI
2-benzoyl-4-oxo-7-isopropyl-HPI
2-benzoyl-4-oxo-7-n-butyl-HPI 2-benzoyl-4-oxo-7-isobutyl-HPI
2-benzoyl-4-oxo-7-sec.-butyl-HPI
2-benzoyl-4-oxo-7-tert.-butyl-HPI
2-benzoyl-4-oxo-8-methyl-HPI
2-benzoyl-4-oxo-8-ethyl-HPI
2-benzoyl-4-oxo-9 -methyl-HPI; m.p. 162° – 163° C.
2-benzoyl-4-oxo-9-ethyl-HPI
2-benzoyl-4-oxo-10-methyl-HPI
2-benzoyl-4-oxo-10-ethyl-HPI
2-benzoyl-4-oxo-11-methyl-HPI
2-benzoyl-4-oxo-11-ethyl-HPI
2-benzoyl-4-oxo-11b-methyl-HPI
2-benzoyl-4-oxo-11b-ethyl-HPI
2-benzoyl-4-oxo-9,10-dimethoxy-HPI; m.p. 130° C.
2-benzoyl-4-oxo-9,10-diethoxy-HPI
2-benzoyl-4-oxo-9,10-diacetoxy-HPI
2-benzoyl-4-oxo-9,10-dibenzoyloxy-HPI
1-methyl-2-(3-fluorobenzoyl)-4-oxo-HPI
2-(3-fluorobenzoyl)-3-methyl-4-oxo-HPI
2-(3-fluorobenzoyl)-4-oxo-6-cis-methyl-HPI
2-(3-fluorobenzoyl)-4-oxo-6-trans-methyl-HPI
2-(3-fluorobenzoyl)-4-oxo-7-methyl-HPI
2-(3-fluorobenzoyl)-4-oxo-8-methyl-HPI
2-(3-fluorobenzoyl)-4-oxo-9-methyl-HPI
2-(3-fluorobenzoyl)-4-oxo-10-methyl-HPI
2-(3-fluorobenzoyl)-4-oxo-11-methyl-HPI
2-(3-fluorobenzoyl)-4-oxo-11b-methyl-HPI
1-methyl-2-(4-fluorobenzoyl)-4-oxo-HPI
2-(4-fluorobenzoyl)-3-methyl-4-oxo-HPI
2-(4-fluorobenzoyl)-4-oxo-6-cis-methyl-HPI
2-(4-fluorobenzoyl)-4-oxo-6-trans-methyl-HPI; m.p. 158° C.
2-(4-fluorobenzoyl)-4-oxo-7-methyl-HPI
2-(4-fluorobenzoyl)-4-oxo-8-methyl-HPI
2-(4-fluorobenzoyl)-4-oxo-9-methyl-HPI
2-(4-fluorobenzoyl)-4-oxo-10-methyl-HPI
2-(4-fluorobenzoyl)-4-oxo-11-methyl-HPI
2-(4-fluorobenzoyl)-4-oxo-11b-methyl-HPI b. 15 g. boron tribromide are added dropwise at 5° – 10° C. to 6 g. 2-benzoyl-4-oxo-9,10-dimethoxy-HPI in 100 ml. dichloromethane, whereafter the reaction mixture is stirred for an hour at 20° C. and then poured onto ice. The crystals which separate out are washed with water, dissolved in 200 ml. hot methanol and mixed with 50 ml. 12.5% hydrochloric acid. After an hour, the reaction mixture is evaporated and worked up as usual. There is obtained 2-benzoyl-4-oxo-9,10-dihydroxy-HPI which, after recrystallization from methanol, melts at 140° C.

c. 5.5 g. 2-benzoyl-4-oxo-9,10-dibenzoyloxy-HPI are stirred in 200 ml. 10% aqueous sodium hydroxide solution for 12 hours at 20° C., insoluble material is then filtered off and the filtrate is then acidified with hydrochloric acid and worked up as usual to give 2-benzoyl-4-oxo-9,10-dihydroxy-HPI, which melts at 140° C.

d. 3.4 g. 2-benzoyl-4-oxo-9,10-dihydroxy-HPI in 100 ml. methanol are mixed with an excess of ethereal diazomethane solution until a pale yellow coloration remains, whereafter the reaction mixture is evaporated to give 2-benzoyl-4-oxo-9,10-dimethoxy-HPI which, after recrystallization from ethanol/ether, melts at 130° C.

e. 1.15 g. sodium borohydride is added portionwise at 0° C. to 6.8 g. 2-(4-oxo-cyclohexylcarbonyl)-4-oxo-6cis-methyl-HPI in 100 ml. ethanol, whereafter the reaction mixture is stirred for 12 hours at 20° C. and then poured on to ice. There is thus obtained 2-(4-hydroxycyclohexylcarbonyl)-4-oxo-6-cis-methyl-HPI in the form of an amorphous isomeric mixture.

f. 6.8 g. 2-(4-oxo-cyclohexylcarbonyl)-4-oxo-6trans-methyl-HPI in 100 ml. methanol are hydrogenated in the presence of 2 g. Raney nickel for 2 hours at 50° C. and 100 atms. pressure and then filtered and the filtrate is evaporated to give 2-(4-hydroxycyclohexylcarbonyl)-4-oxo6-trans-methyl-HPI in the form of an amorphous isomeric mixture.

g. 3.4 g. 2-(4-oxo-cyclohexylcarbonyl)-4-oxo-6trans-methyl-HPI, 0.2 ml. water, 3.2 g. sulfur tetrafluoride and 50 ml. dichloromethane are shaken in an autoclave for 24 hours at 30° C., whereafter the reaction mixture is poured into a dilute aqueous solution of sodium carbonate and worked up as usual to give 2-(4,4-difluorocyclohexylcarbonyl)-4-oxo-6-trans-methyl-HPI.

h. 135 g. 2-benzoyl-4-oxo-6-cis-methyl-HPI are boiled in 1.5 liters 25% hydrochloric acid and 100 ml. methanol for 12 hours, whereafter the reaction mixture is cooled, the benzoic acid which separates out is filtered off and the filtrate is washed with diethyl ether. The crude product obtained after working up in the usual way is heated for 2 hours at 16 mm.Hg. at 200° C. and the reaction mixture, after cooling, is dissolved in water and washed with ether. The aqueous phase is reduced alkaline, extracted with chloroform and worked up as usual. There is obtained 4-oxo-6-cis-methyl-HPI which, after recrystallization from benzene/petroleum ether, melts at 119° – 120° C.

EXAMPLE 2 a. 1-carboxymethylaminomethyl-3-cis-methyl-1,2,3,4-tetrahydroisoquinoline hydrochloride (obtained by the reaction of 1-aminomethyl-3-cis-methyl-1,2,3,4-tetrahydroisoquinoline monohydrochloride with chloroacetic acid in dimethylformamide) is heated for 2 hours at 12 mm.Hg. at 195° C., then cooled, dissolved in water, washed with ether and rendered alkaline. After extraction with chloroform and the usual working up, there is obtained 4-oxo-6-cismethyl-HPI, which melts at 119 – 120° C.

The following compounds are obtained analogously by ring closure of the appropriate tetrahydroisoquinolines:

1-methyl-4-oxo-HPI
1-ethyl-4-oxo-HPI
3-methyl-4-oxo-HPI
3-ethyl-4-oxo-HPI
3-n-propyl-4-oxo-HPI
3-isopropyl-4-oxo-HPI
3-n-butyl-4-oxo-HPI
3-isobutyl-4-oxo-HPI
3-tert-butyl-4-oxo-HPI
4-oxo-6-trans-methyl-HPI; m.p. 135° – 136° C.
4-oxo-6-cis-ethyl-HPI
4-oxo-6-trans-ethyl-HPI
4-oxo-6-cis-n-propyl-HPI
4-oxo-6-trans-n-propyl-HPI
4-oxo-6-isopropyl-HPI
4-oxo-6-trans-isopropyl-HPI
4-oxo-6-cis-n-butyl-HPI
4-oxo-6-trans-n-butyl-HPI
4-oxo-6-cis-isobutyl-HPI
4-oxo-6-trans-isobutyl-HPI
4-oxo-6-cis-sec.-butyl-HPI
4-oxo-6-trans-sec.-butyl-HPI 4-oxo-6-cis-tert.-butyl-HPI
4-oxo-6-trans-tert.-butyl-HPI
4-oxo-7-methyl-HPI
4-oxo-7-ethyl-HPI
4-oxo-8-methyl-HPI
4-oxo-8-n-butyl-HPI
4-oxo-8-hydroxy-HPI
4-oxo-8-methoxy-HPI
4-oxo-8-amino-HPI
4-oxo-8-methylamino-HPI
4-oxo-8-dimethylamino-HPI
4-oxo-8-nitro-HPI
4-oxo-8-fluoro-HPI
4-oxo-8-chloro-HPI
4-oxo-9-methyl-HPI
4-oxo-9-hydroxy-HPI
4-oxo-9-methoxy-HPI
4-oxo-9-amino-HPI
4-oxo-9-methylamino-HPI
4-oxo-9-dimethylamino-HPI
4-oxo-9-nitro-HPI
4-oxo-9-fluoro-HPI 4-oxo-9-chloro-HPI
4-oxo-10-methyl-HPI
4-oxo-10-hydroxy-HPI
4-oxo-10-methoxy-HPI
4-oxo-10-amino-HPI
4-oxo-10-methylamino-HPI
4-oxo-10-dimethylamino-HPI
4-oxo-10-nitro-HPI
4-oxo-10-fluoro-HPI
4-oxo-10-chloro-HPI
4-oxo-11-methyl-HPI
4-oxo-11-hydroxy-HPI
4-oxo-11-methoxy-HPI
4-oxo-11-amino-HPI
4-oxo-11-methylamino-HPI
4-oxo-11-dimethylamino-HPI
4-oxo-11-nitro-HPI
4-oxo-11-fluoro-HPI
4-oxo-11-chloro-HPI
4-oxo-11b-methyl-HPI
4-oxo-11b-ethyl-HPI b. 5.5 g. 4-nitrobenzoyl chloride in 100 ml. chloroform are added to 5 g. 4-oxo-6-cis-methyl-HPI and 6 ml. triethylamine in 100 ml. chloroform, whereby the temperature increases to 50° C. After an hour, the reaction mixture is washed with water and then worked up as usual to give 2-(4-nitrobenzoyl)-4-oxo-6-cis-methyl-HPI which, after recrystallization from ethanol, melts at 225° – 226° C.

The following compounds are obtained analogously by acylating the appropriate compounds which are unsubstituted in the 2-posiion:

1-methyl-2-(3-nitrobenzoyl)-4-oxo-HPI
2-(3-nitrobenzoyl)-3-methyl-4-oxo-HPI
2-(3-nitrobenzoyl)-4-oxo-6-cis-methyl-HPI; m.p. 184°–185° C.
2-(3-nitrobenzoyl)-4-oxo-6-trans-methyl-HPI; m.p. 90° – 92° C.
2-(3-nitrobenzoyl)-4-oxo-7-methyl-HPI
2-(3-nitrobenzoyl)-4-oxo-8-methyl-HPI
2-(3-nitrobenzoyl)-4-oxo-8-nitro-HPI
2-(3-nitrobenzoyl)-4-oxo-8-fluoro-HPI
2-(3-nitrobenzoyl)-4)-oxo-8-chloro-HPI
2-(3-nitrobenzoyl)-4-oxo-9-methyl-HPI
2-(3-nitrobenzoyl)-4-oxo-9-nitro-HPI
2-(3-nitrobenzoyl)-4-oxo-9-fluoro-HPI
2-(3-nitrobenzoyl)-4-oxo-9-chloro-HPI
2-(3-nitrobenzoyl)-4-oxo-10-methyl-HPI
2-(3-nitrobenzoyl)-4-oxo-10-nitro-HPI
2-(3-nitrobenzoyl)-4-oxo-10-fluoro-HPI
2-(3-nitrobenzoyl)-4-oxo-10-chloro-HPI
2-(3-nitrobenzoyl)-4-oxo-11-methyl-HPI
2-(3-nitrobenzoyl)-4-oxo-11-nitro-HPI
2-(3-nitrobenzoyl)-4-oxo-11-fluoro-HPI
2-(3-nitrobenzoyl)-4-oxo-11-chloro-HPI
2-(3-nitrobenzoyl)-4-oxo-11b-methyl-HPI
1-methyl-2-(4-nitrobenzoyl)-4-oxo-HPI
2-(4-nitrobenzoyl)-3-methyl-4-oxo-HPI
2-(4-nitrbenzoyl)-4-oxo-6-trans-methyl-HPI
2-(4-nitrobenzoyl)-4-oxo-7-methyl-HPI
2-(4-nitrobenzoyl)-4-oxo-8-methyl-HPI
2-(4-nitrobenzoyl)-4-oxo-8-nitro-HPI
2-(4-nitrobenzoyl)-4-oxo-8-fluoro-HPI
2-(4-nitrobenzoyl)-4-oxo-8-chloro-HPI
2-(4-nitrobenzoyl)-4-oxo-9-methyl-HPI
2-(4-nitrobenzoyl)-4-oxo-9-nitro-HPI
2-(4-nitrobenzoyl)-4-oxo-9-fluoro-HPI
2-(4-nitrobenzoyl)-4-oxo-9-chloro-HPI
2-(4-nitrobenzoyl)-4-oxo-10-methyl-HPI
2-(4-nitrobenzoyl)-4-oxo-10-nitro-HPI
2-(4-nitrobenzoyl)-4-oxo-10-fluoro-HPI
2-(4-nitrobenzoyl)-4-oxo-10-chloro-HPI
2-(4-nitrobenzoyl)-4-oxo-11-methyl-HPI
2-(4-nitrobenzoyl)-4-oxo-11-nitro-HPI
2-(4-nitrobenzoyl)-4-oxo-11-fluoro-HPI
2-(4-nitrobenzoyl)-4-oxo-11-chloro-HPI
2-(4-nitrobenzoyl)-4-oxo-11b-methyl-HPI
1-methyl-2-(2-fluorobenzoyl)-4-oxo-HPI
2-(2-fluorobenzoyl)-3-methyl-4-oxo-HPI
2-(2-fluorobenzoyl)-4-oxo-6-cis-methyl-HPI
2-(2-fluorobenzoyl)-4-oxo-6-trans-methyl-HPI
2-(2-fluorobenzoyl)-4-oxo-7-methyl-HPI
2-(2-fluorobenzoyl)-4-oxo-8-methyl-HPI
2-(2-fluorobenzoyl)-4-oxo-8-nitro-HPI
2-(2-fluorobenzoyl)-4-oxo-8-fluoro-HPI
2-(2-fluorobenzoyl)-4-oxo-8-chloro-HPI
2-(2-fluorobenzoyl)-4-oxo-9-methyl-HPI
2-(2-fluorobenzoyl)-4-oxo-9-nitro-HPI
2-(2-fluorobenzoyl)-4-oxo-9-fluoro-HPI
2-(2-fluorobenzoyl)-4-oxo-9-chloro-HPI
2-(2-fluorobenzoyl)-4-oxo-10-methyl-HPI
2-(2-fluorobenzoyl)-4-oxo-10-nitro-HPI 2-(2-fluorobenzoyl)-4-oxo-10-fluoro-HPU
2-(2-fluorobenzoyl)-4-oxo-10-chloro-HPI
2-(2-fluorobenzoyl)-4-oxo-11-methyl-HPI
2-(2-fluorobenzoyl)-4-oxo-11-nitro-HPI
2-(2-fluorobenzoyl)-4-oxo-fluoro-HPI
2-(2-fluorobenzoyl)-4-oxo-11-chloro-HPI
2-(2-fluorobenzoyl)-4-oxo-11b-methyl-HPI
1-methyl-2-(3-fluorobenzoyl)-4-oxo-HPI
2-(3-fluorobenzoyl)-3-methyl-4-oxo-HPI
2-(3-fluorobenzoyl)-4-oxo-6-cis-methyl-HPI
2-(3-fluorobenzoyl)-4-oxo-6-trans-methyl-HPI
2-(3-fluorobenzoyl)-4-oxo-7-methyl-HPI
2-(3-fluorobenzoyl)-4-oxo-7-methyl-HPI
2-(3-fluorobenzoyl)-4-oxo-8-methyl-HPI
2-(3-fluorobenzoyl)-4-oxo-8-nitro-HPI
2-(3-fluorobenzoyl)-4-oxo-8-fluoro-HPI
2-(3-fluorobenzoyl)-4-oxo-8-chloro-HPI
2-(3-fluorobenzoyl)-4-oxo-9-nitro-HPI
2-(3-fluorobenzoyl)-4-oxo-9-fluoro-HPI
2-(3-fluorobenzoyl)-4-oxo--chloro-HPI
2-(3-fluorobenzoyl)-4-oxo-10-nitro-HPI 2-(3-fluorobenzoyl)-4-oxo-10-fluoro-HPI
2-(3-fluorobenzoyl)-4-oxo-10-chloro-HPI
2-(3-fluorobenzoyl)-4-oxo-11-nitro-HPI
2-(3-fluorobenzoyl)-4-oxo-11-fluoro-HPI
2-(3-fluorobenzoyl)-4-oxo-11-chloro-HPI
2-(4-fluorobenzoyl)-4-oxo-8-nitro-HPI
2-(4-fluorobenzoyl)-4-oxo-8-fluoro-HPI
2-(4-fluorobenzoyl)-4-oxo-8-chloro-HPI
2-(4-fluorobenzoyl)-4-oxo-9-nitro-HPI
2-(4-fluorobenzoyl-4-oxo-9-fluoro-HPI
2-(4-fluorobenzoyl)-4-oxo-9-chloro-HPI
2-(4-fluorobenzoyl)-4-oxo-10-nitro-HPI
2-(4-fluorobenzoyl)-4-oxo-10-fluoro-HPI
2 -(4-fluorobenzoyl)-4-oxo-10-chloro-HPI
2-(4-fluorobenzoyl)-4-oxo-11-nitro-HPI
2-(4-fluorobenzoyl)-4-oxo-11-fluoro-HPI
2-(4-fluorobenzoyl)-4-oxo-11-chloro-HPI
2-(tetrahydropyranyl-4-carbonyl)-4-oxo-8-nitro-HPI
2-(tetrahydropyranyl-4-carbonyl)-4-oxo-8-fluoro-HPI
2-(tetrahydropyranyl-4-carbonyl)-4-oxo-8-chloro-HPI
2-(tetrahydropyranyl-4-carbonyl)-4-oxo-9-nitro-HPI
2-(tetrahydropyranyl-4-carbonyl)-4-oxo-9-fluoro-HPI
2-(tetrahydropyranyl-4-carbonyl)-4-oxo-9-chloro-HPI
2-(tetrahydropyranyl-4-carbonyl)-4-oxo-10-nitro-HPI
2-(tetrahydropyranyl-4-carbonyl)-4-oxo-10-fluoro-HPI
2-(tetrahydropyranyl-4-carbonyl)-4-oxo-10-chloro-HPI
2-(tetrahydropyranyl-4-carbonyl)-4-oxo-11-nitro-HPI
2-(tetrahydropyranyl-4-carbonyl)-4-oxo-11-fluoro-HPI
2-(tetrahydropyranyl-4-carbonyl)-4-oxo-11-chloro-HPI
2-(thiacyclohexyl-4-carbonyl)-4-oxo-8-nitro-HPI
2-(thiacyclohexyl-4-carbonyl)-4-oxo-8-fluoro-HPI
2-(thiacyclohexyl-4-carbonyl)-4-8-chloro-HPI
2-(thiacyclohexyl-4-carbonyl)-4-oxo-9-nitro-HPI
2-(thiacyclohexyl-4-carbonyl)-4-oxo-9-fluoro-HPI
2-(thiacyclohexyl-4-carbonyl)-4-oxo-9-chloro-HPI
2-(thiacyclohexyl-4-carbonyl)-4-oxo-10-nitro-HPI
2-(thiacyclohexyl-4-carbonyl)-4-oxo-10-fluoro-HPI
2-(thiacyclohexyl-4-carbonyl)-4-oxo-10-chloro-HPI
2-(thiacyclohexyl-4-carbonyl)-4-oxo-11-nitro-HPI
2-(thiacyclohexyl-4-carbonyl)-4-oxo-11-fluoro-HPI
2-(thiacyclohexyl-4-carbonyl)-4-oxo-11-chloro-HPI c. 2.4 g. thionyl chloride are added dropwise at −40° C. to a solutin of 2.9 g. cyclohexanone-4-carboxylic acid in 20 ml. dimethylformamide and 50 ml. dichloromethane, whereafter the reaction mixture is stirred for 30 minutes and then 4.3 g 4-oxo-6-trans-methyl-HPI and 4.1 g. triethylamine in 50 ml. dichloromethane are added thereto, followed by stirring for one hour and thereafter working up as usual. There is obtained 2-(4-oxo-cyclohexylcarbonyl)-4-oxo-6-trans-methyl-HPI which, after recrystallization from diethyl ether, melts at 118° – 120° C.

The following compounds are obtained in an analogous manner by acrylation of the appropriate compounds:

1-methyl-2-(cyclohexene-4-carbonyl)-4-oxo-HPI
2-(cyclohexene-4-carbonyl)-3-methyl-4-oxo-HPI
2-(cyclohexene-4-carbonyl)-4-oxo-6-cis-methyl-HPI
2-(cyclohexene-4-carbonyl)-4-oxo-6-trans-methyl-HPI
2-(cyclohexene-4-carbonyl)-4-oxo-7-methyl-HPI
2(cyclohexene-4-carbonyl)-4-oxo-8-methyl-HPI
2-(cyclohexene-4-carbonyl)-4-oxo-8-methyl-HPI
2-(cyclohexene-4-carbonyl)-4-oxo-9-methyl-HPI
2-(cyclohexene-4-carbonyl)-4-oxo-10-methyl-HPI
2-(cyclohexene-4-carbonyl)-4-oxo-11methyl-HPI
2-(cyclohexene-4-carbonyl)-4-oxo-11b-methyl-HPI d. 1 ml. phosphorus trichloride is added dropwise at 140° C. to a solution of 6.5 g. 4-oxo-6-trans-methyl-HPI and 5 g. 3-nitrobenzoic acid in 50 ml. chlorobenzene. The reaction mixture is boiled for an hour, then evaporated and the residue chromatographed over silica gel with chloroform as elution agent to give 2-(3-nitrobenzoyl)-4-oxo-6-trans-methyl-HPI, which melts at 90° – 92° C.

The following compounds are obtained analogously by acylation of the appropriate compounds:

1-methyl-2nicotinoyl-4-oxo-HPI
2-nicotinoyl-3-methyl-4-oxo-HPI
2-nicotinoyl-4-oxo-6-cis-methyl-HPI
2-nicotinoyl-4-oxo-6-trans-methyl-HPI
2-nicotinoyl-4-oxo-7-methyl-HPI
2-nicotinoyl-4-oxo-8-methyl-HPI
2-nicotinoyl-4-oxo-9-methyl-HPI
2-nicotinoyl-4-oxo-10-methyl-HPI
2-nicotinoyl-4-oxo-11-methyl-HPI
2-nicotinoyl-4-oxo-11b-methyl-HPI
1-methyl-2-(2-thienylcarbonyl)-4-oxo-HPI
2-(2-thienylcarbonyl)-3-methyl-4-oxo-HPI
2-(2-thienylcarbonyl)-4-oxo-6-cis-methyl-HPI
2-(2-thienylcarbonyl)-4-oxo-6-trans-methyl-HPI
2-(2-thienylcarbonyl)-4-oxo-7-methyl-HPI
2-(2-thienylcarbonyl)-4-oxo-8-methyl-HPI
2-(2-thienylcarbonyl)-4-oxo-9-methyl-HPI
2-(2-thienylcarbonyl)-4-oxo-10-methyl-HPI
2-(2-thienylcarbonyl)-4-oxo-11-methyl-HPI
2-(2-thienylcarbonyl)-4-oxo-11b-methyl-HPI
1-methyl-2-(3-thienylcarbonyl)-4-oxo-HPI
2-(3-thienylcarbonyl)-3-methyl-4-oxo-HPI
2-(3-thienylcarbonyl)-4-oxo-6-cis-methyl-HPI
2-(3-thienylcarbonyl)-4-oxo-6-trans-methyl-HPI
2-(3-thienylcarbonyl)-4-oxo-7-methyl-HPI
2-(3-thienylcarbonyl)-4-oxo-8-methyl-HPI
2-(3-thienylcarbonyl)-4-oxo-9-methyl-HPI
2-(3-thienylcarbonyl)-4-oxo-10-methyl-HPI
2-(3-thienylcarbonyl)-4-oxo-11-methyl-HPI
2-(3-thienylcarbonyl)-4-oxo-11b-methyl-HPI e. A solution of 6.5 g. 4-oxo-6-cis-methyl-HPI, 4.8 g. isobutyric acid anhydride and 2.2 g. triethylamine in 100 ml. dichloromethane is left to stand overnight at 20° C., whereafter the reaction mixture is worked up as usual to give 2-isobutyryl-4-oxo-6-cis-methyl-HPI, which melts at 136° C.

f. 5 g. 4-oxo-6-cis-methyl-HPI, 4 g. 3-nitrobenzoic acid and 3 g. silicon tetrachloride in 100 m. pyridine are boiled for an hour, then poured on to ice and worked up as usual to give 2-(3-nitrobenzyl)-4-oxo-6-cis-methyl-HPI, which melts at 184°–185° C.

g. 3.3 g. (2-cyclohexane-4-carbonyl)-4-oxo-6-trans-methyl-HPI in 100 ml. tetrahydrofuran are hydrogenated on 0.3 g. platinum oxide at 20° C. and at atmospheric pressure, whereafter the solvent is distilled off to give 2-cyclohexylcarbonyl-4-oxo-6-trans-methyl-HPI, which melts at 134° C.

EXAMPLE 3

Crude 1-(N-benzoyl-N-carboxymethylaminomethyl)-4-methyl-1,2,3,4-tetrahydroisoquinoline, obtained by the reaction of 1.4 g. 2-phenylpropylamine with 2.7 g. N-(2,2-dimethoxyethyl)-N-carboxymethylbenzamide (obtainable by the reaction of trimethylsilyl hippurate with trimethylsilyl chloride/triethylamine and chloroacetaldehyde dimethyl acetal) in 20 ml. concentrated hydrochloride at 70° C., is boiled overnight with toluene for the removal of water. Upon cooling, 2-benzoyl-4-oxo-7-methyl-HPI crystallizes out. It melts at 157° C.

In an analogous manner, from 1-(N-benzoyl-N-carboxymethylaminoethyl)-4-phenyl-1,2,3,4-tetrahydroisoquinoline (obtainable from 2,2-diphenylethylamine), there is obtained 2-benzoyl-4-oxo-7-phenyl-HPI.

EXAMPLE 4

3.4 g. 1-benzoyl-3-oxo-4-(2-hydroxyethyl)-5-p-tolyl-piperazine (obtainable by the reaction of p-tolylglyoxal bisulfite adduct with aminomalondiamide to give 2-aminocarbonyl-3-hydroxy-5-p-tolylpyrazine, saponification and decarboxylation to 3-hydroxy-5-p-tolylpyrazine, hydrogenation to 3-oxo-5-p-tolylpiperazine, reaction with benzoyl chloride to give 1-benzoyl-3-oxo-5-p-tolylpiperazine and reaction with ethylene oxide in the presence of sodium hydroxide) in about 50 ml. liquid hydrogen fluoride is left to stand for 3 days at 20° C., whereafter the reaction mixture is poured into ice water and then worked up as usual to give 2-benzoyl-4-oxo-9-methyl-HPI, which has a melting point of 162°–163° C.

EXAMPLE 5

3.6 g. 1-benzoyl-3-oxo-4-(2-chloroethyl)-5-p-tolylpiperazine (obtainable from 1-benzoyl-3-oxo-4-(2-hydroxyethyl)-5-p-tolylpiperazine by reaction with thionyl chloride) in 50 ml. carbon disulfide are added, with ice cooling, to 0.5 g. aluminum trichloride in 50 ml. carbon disulfide. The reaction mixture is stirred for 12 hours, then poured on to ice and worked up as usual to give 2-benzoyl-4-oxo-9-methyl-HPI, which melts at 162°–163° C.

EXAMPLE 6 a. 3.37 g. 1-benzoyl-3-oxo-5-phenyl-piperazinyl-4-acetic acid are dissolved in 15 ml. liquid hydrogen fluoride, wherafter the solution is left to stand for 2 days, then poured on to ice. After the usual working up, there is obtained 2-benzoyl-4,7-dioxo-HPI.

b. 3.2 g. 2-benzoyl-4,7-dioxo-HPI are dissolved in 60 ml. methanol, 0.5 g. sodium borohydride is added thereto portionwise at 0° C. and the reaction mixture is stirred for 12 hours at 20° C. and poured on to ice. There is thus obtained 2-benzoyl-4-oxo-7-hydroxy-HPI.

c. 3.22 g. 2-benzoyl-4-oxo-7-hydroxy-HPI are dissolved in 20 ml. chloroform and subsequently 1.3 g. thionyl chloride in 5 ml. chloroform added thereto dropwise, while stirring. The reaction mixture is boiled for an hour, then evaporated and, after the usual working up, there is obtained 2-benzoyl-4-oxo-7-chloro-HPI.

EXAMPLE 7 a. 3.70 g. 1-benzoyl-3-oxo-4-chlorocarbonylmethyl-5-p-tolyl-piperazine are dissolved in 50 ml. nitrobenzene, 1.4 g. aluminium trichloride are added thereto and the reaction mixture is stirred overnight at 20° C., whereafter, after the usual working up, there is obtained 2-benzoyl-4,7-dioxo-9-methyl-HPI.

b. 3.34 g. 2-benzoyl-4,7-dioxo-9-methyl-HPI, 1.5 g. potassium hydroxide, 3 ml. 35% hydrazine and 25 ml. diethylene glycol are heated to 100° C. for an hour and the temperature is then slowly increased until the hydrazone formed is destroyed, whereby excess hydrazine and water evaporate off, whereafter the reaction mixture is boiled for 4 hours. The reaction mixture is then cooled and, after the usual working up, there is obtained 2-benzoyl-4-oxo-9-methyl-HPI, which melts at 162°–163° C.

c. 3.6 g. 2-benzoyl-4-oxo-7-chloro-9-methyl-HPI (obtainable by the hydrogenation of 2-benzoyl-4,7-dioxo-9-methyl-HPI in the presence of Raney nickel to give 2-benzoyl-4-oxo-7-hydroxy-9-methyl-HPI and subsequent reaction with thionyl chloride) are hydrogenated in 100 ml. methanol and in the presence of 0.3 g. palladium charcoal at 20° C. and at atmospheric pressure, whereafter the solution is concentrated. After the solution of diethyl ether, there is obtained 2-benzoyl-4-oxo-9-methyl-HPI, which melts at 162°–163° C.

EXAMPLE 8

3.2 g. 2-benzoyl-4-oxo-9-methyl-2,3,6,7-tetrahydro-4H-pyrazino[2,1-a]isoquinoline (obtainable by the cyclization of 1-(2-m-tolylethyl)-4-benzoyl-piperazine-2,6-dione with polyphosphoric acid) are hydrogenated in 200 ml. methanol in the presence of 1.5 g. Raney nickel at 20° C. and at atmospheric pressure. After evaporation of the solvent, there is obtained 2-benzoyl-4-oxo-9-methyl-HPI, which melts at 162°–163° C.

EXAMPLE 9

3.2 g. 2-benzoyl-4-oxo-7-methylene-HPI (obtainable from 3-hydroxy-5-phenyl-pyrazine by hydrogenation to give 3-oxo-5-phenyl-piperazine, reaction with benzoyl chloride to give 1-benzoyl-3-oxo-5-phenyl-piperazine, reaction with trimethylsilyl chloride/triethylamine and trimethylsilyl chloroacetate to give 1-benzoyl-3-oxo-5-phenyl-piperazinyl-4-acetic acid, cyclization with hydrogen fluoride to give 2-benzoyl-4,7-dioxo-HPI and reaction with methylene triphenyl phosphorane in diethyl ether) are hydrogenated in 100 ml. ethanol in the presence of 1 g. 5% palladium charcoal at 40° C. and at atmospheric pressure and then filtered and the filtrate evaporated to give 2-benzoyl-4-oxo-7-methyl-HPI, which melts at 157° C.

EXAMPLE 10

3.2 g. 2-benzoyl-4-oxo-9-methyl-1,2,3,11b-tetrahydro-4H-pyrazino[2,1-a]isoquinoline (obtainable from 1-benzoyl-3-oxo-5-p-tolyl-piperazine by reaction with trimethylsilyl cloride/triethylamine and trimethylsilyl chloroacetate to give 1-benzoyl-3-oxo-4-carboxymethyl-5-p-tolyl-piperazine, reaction with liquid hydrogen fluoride to give 2-benzoyl-4,7-dioxo-9-methyl-HPI and reaction with trimethylsilyl chloride/zinc in diethyl ether) are hydrogenated in 50 ml. tetrahydrofuran in the presence of 200 mg. platinum oxide at 20° C. and at atmospheric pressure, followed by filtration and evaporation of the filtrate to give 2-benzoyl-4-oxo-9-methyl-HPI, which melts at 162°–163° C.

EXAMPLE 11

5.7 g. 3-chloroperbenzoic acid are added portionwise to 4.6 g. 2-(pyridyl-2-carbonyl)-4-oxo-HPI in 270 ml. dichloromethane and the reaction mixture then left to stand for 24 hours at 20° C. Ammonia is then passed in, the reaction mixture is filtered with suction and the solvent is evaporated off from the filtrate to give 1-hydroxy-2-(pyridyl-2-carbonyl)-4-oxo-HPI which, after recrystallization from acetone, melts at 140° C.

EXAMPLE 12

76.5 g. 2-benzoyl-4-oxo-HPI in 1 liter anhydrous tetrahydrofuran are added dropwise to a suspension of sodamide, prepared from 5.75 g. sodium in 1250 ml.

liquid ammonia, whereafter the reaction mixture is stirred for an hour, 32 ml. ethylene oxide are added thereto and the reaction mixture is stirred overnight. It is then allowed to come to ambient temperature and the solvent is distilled off. After the usual working up, there is obtained a resin which is chromatographically purified over silica gel, using chloroform as elution agent. There is obtained 2-benzoyl-3-(2-hydroxyethyl)-4-oxo-HPI which, after recrystallization from ethyl acetate/diethyl ether, melts at 194° C.

EXAMPLE 13

3.12 g. 2-cyclohexylcarbonyl-4-oxo-HPI are dissolved in 50 ml. chloroform, a solution of 1.6 g. bromine in 20 ml. chloroform is added dropwise thereto, while stirring, at 20° C. and the reaction mixture is stirred overnight. After the usual working up, there is obtained 2-cyclohexylcarbonyl-4-oxo-8(?)-bromo-HPI (the position of the bromine atom is not definite). Other bromination products are thereby also formed.

EXAMPLE 14 a. A solution of 31.2 g. 2-cyclohexylcarbonyl-4-oxo-HPI in 50 ml. acetic acid is added to 10° C. to 100 g. of fuming sulfuric acid (30% by weight of sulfur trioxide), cooled to 0° C. and 5 ml. nitric acid (D = 1.52) in 10 ml. acetic acid added dropwise thereto at a temperature below 20° C. The reaction mixture is stirred for an hour at 10°–20° C., hydrolyzed with ice water and extracted with chloroform. The chloroform extract is purified chromatographically on silica gel, using ethyl acetate as elution agent. There is obtained 2-cyclohexylcarbonyl-4-oxo-11(or 8)-nitro-HPI ($R_f$ value about 0.4) and 2-cyclohexylcarbonyl-4-oxo-8(or 11)-nitro-HPI ($R_f$ value 0.25). Both compounds exhibit infra-red bands at 1660, 1530, 1350 and 750 cm$^{-1}$ and mass peaks at m/e = 246; 357.

The following compounds are obtained analogously by the nitration of the corresponding compounds which are unsubstituted in the 8- and 11-positions:

1-methyl-2-cyclohexylcarbonyl-4-oxo-8(or 11)-nitro-HPI
1-methyl-2-cyclohexylcarbonyl-4-oxo-11(or 8)-nitro-HPI
2-cyclohexylcarbonyl-3-methyl-4-oxo-8(or 11)-nitro-HPI
2-cyclohexylcarbonyl-3-methyl-4-oxo-11(or 8)-nitro-HPI
2-cyclohexylcarbonyl-4-oxo-6-cis-methyl-8(or 11)-nitro-HPI
2-cyclohexylcarbonyl-4-oxo-6-cis-methyl 11(or 8) nitro-HPI
2-cyclohexylcarbonyl-4-oxo-6-trans-methyl-8(or 11)-nitro-HPI
2-cyclohexylcarbonyl-4-oxo-6-trans-methyl-11(or 8)-nitro-HPI
2-cyclohexylcarbonyl-4-oxo-7-methyl-8(or 11)-nitro-HPI
2-cyclohexylcarbonyl-4-oxo-7-methyl-11(or 8)-nitro-HPI
2-cyclohexylcarbonyl-4-oxo-8(or 11)-nitro-9-methyl-HPI
2-cyclohexylcarbonyl-4-oxo-9-methyl-11(or 8)-nitro-HPI
2-cyclohexylcarbonyl-4-oxo-8(or 11)-nitro-10-methyl-HPI
2-cyclohexylcarbonyl-4-oxo-10-methyl-11(or 8)-nitro-HPI
2-cyclohexylcarbonyl-4-oxo-8(or 11)-nitro-11b-methyl-HPI
2-cyclohexylcarbonyl-4-oxo-11(or 8)-nitro-11b-methyl-HPI
1-methyl-2-(tetrahydropyranyl-4-carbonyl)-4-oxo-8(or 11)-nitro-HPI
1-methyl-2-(tetrahydropyranyl-4-carbonyl)-4-oxo-11(or 8)-nitro-HPI
2-(tetrahydropyranyl-4-carbonyl)-3-methyl-4-oxo-8(or 11)-nitro-HPI
2-(tetrahydropyranyl-4-carbonyl)-3-methyl-4-oxo-11(or 8)-nitro-HPI
2-(tetrahydropyranyl-4-carbonyl)-4-oxo-6-cis-methyl-8(or 11)-nitro-HPI
2-(tetrahydropyranyl-4-carbonyl)-4-oxo-6-cis-methyl-11(or 8)-nitro-HPI
2-(tetrahydropyranyl-4-carbonyl)-4-oxo-6-trans-methyl-8(or 11)-nitro-HPI
2-(tetrahydropyranyl-4-carbonyl)-4-oxo-6-trans-methyl-11(or 8)-nitro-HPI
2-(tetrahydropyranyl-4-carbonyl)-4-oxo-7-methyl-8(or 11)-nitro-HPI
2-(tetrahydropyranyl-4-carbonyl)-4-oxo-7-methyl-11(or 8)-nitro-HPI
2-(tetrahydropyranyl-4-carbonyl)-4-oxo-8(or 11)-nitro-9-methyl-HPI
2-(tetrahydropyranyl-4-carbonyl)-4-oxo-9-methyl-11(or 8)-nitro-HPI
2-(tetrahydropyranyl-4-carbonyl)-4-oxo-8(or 11)-nitro-10-methyl-HPI
2-(tetrahydropyranyl-4-carbonyl)-4-oxo-10-methyl-11(or 8)-nitro-HPI
2-(tetrahydropyranyl-4-carbonyl)-4-oxo-8(or 11)-nitro-11b-methyl-HPI
2-(tetrahydropyranyl-4-carbonyl)-4-oxo-11(or 8)-nitro-11b-methyl-HPI
1-methyl-2-(thiacyclohexyl-4-carbonyl)-4-oxo-8(or 11)-nitro-HPI
1-methyl-2-(thiacyclohexyl-4-carbonyl)-4-oxo-11(or 8)-nitro-HPI
2-(thiocyclohexyl-4-carbonyl)-3-methyl-4-oxo-8(or 11)-nitro-HPI
2-(thiacyclohexyl-4-carbonyl)-3-methyl-4-oxo-11(or 8)-nitro-HPI
2-(thiacyclohexyl-4-carbonyl)-4-oxo-6-cis-methyl-8(or 11)-nitro-HPI
2-(thiacyclohexyl-4-carbonyl)-4-oxo-6-cis-methyl-11(or 8)-nitro-HPI
2-(thiacyclohexyl-4-carbonyl)-4-oxo-6-trans-methyl-8(or 11)-nitro-HPI
2-(thiacyclohexyl-4-carbonyl)-4-oxo-6-trans-methyl-11(or 8)-nitro-HPI
2-(thiacyclohexyl-4-carbonyl)-4-oxo-7-methyl-8(or 11)-nitro-HPI
2-(thiacyclohexyl-4-carbonyl)-4-oxo-7-methyl-11(or 8)-nitro-HPI
2-(thiacyclohexyl-4-carbonyl)-4-oxo-8(or 11)-nitro-9-methyl-HPI
2-(thiacyclohexyl-4-carbonyl)-4-oxo-9-methyl-11(or 8)-nitro-HPI
2-(thiacyclohexyl-4-carbonyl)-4-oxo-8(or 11)-nitro-10-methyl-HPI
2-(thiacyclohexyl-4-carbonyl)-4-oxo-10-methyl-11(or 8)-nitro-HPI
2-(thiacyclohexyl-4-carbonyl)-4-oxo-8(or 11)-nitro-11b-methyl-HPI
2-(thiacyclohexyl-4-carbonyl)-4-oxo-11(or 8)-nitro-11b-methyl-HPI 2-benzoyl-4-oxo-8(or 11)-nitro-HPI
2-benzoyl-4-oxo-11(or 8)-nitro-HPI
2-(3-fluorobenzoyl)-4-oxo-8(or 11)-nitro-HPI
2-(3-fluorobenzoyl)-4-oxo-11(or 8)-nitro-HPI
2-(4-fluorobenzoyl)-4-oxo-8(or 11)-nitro-HPI
2-(4-fluorobenzoyl)-4-oxo-11(or 8)-nitro-HPI
2-(3-nitrobenzoyl)-4-oxo-8(or 11)-nitro-HPI
2-(3-nitrobenzoyl)-4-oxo-11(or 8)-nitro-HPI
2-(4-nitrobenzoyl)-4-oxo-8(or 11)-nitro-HPI
2-(4-nitrobenzoyl)-4-oxo-11(or 8)-nitro-HPI b. 4.1 g. 2-cyclohexylcarbonyl-4-oxo-11(or 8)-nitro-HPI are hydrogenated in 100 ml. methanol in the presence of 2 g. 5% palladium charcoal at 20° C. and at atmospheric pressure. After filtration and evaporation of the solvent, the residue is chromatographed on silica gel, using chloroform/methanol (98:2) as elution agent. There is obtained 2-cyclohexylcarbonyl-4-oxo-11(or 8)-amino-HPI which, after recrystallization from benzene/petroleum ether, melts at 160°–162° C.

The following compounds are obtained analogously by hydrogenation of the appropriate nitro compounds:
2-cyclohexylcarbonyl-4-oxo-8(or 11)-amino-HPI
1-methyl-2-(3-aminobenzoyl)-4-oxo-HPI
2-(3-aminobenzoyl)-3-methyl-4-oxo-HPI
2-(3-aminobenzoyl)-4-oxo-6-cis-methyl-HPI hydrochloride; m.p. 195° C.
2-(3-aminobenzoyl)-4-oxo-6-trans-methyl-HPI hydrochloride; m.p. 205° C.
2-(3-aminobenzoyl)-4-oxo-7-methyl-HPI
2-(3-aminobenzoyl)-4-oxo-8-methyl-HPI
2-(3-aminobenzoyl)-4-oxo-8-amino-HPI
2-(3-aminobenzoyl)-4-oxo-8-fluoro-HPI
2-(3-aminobenzoyl)-4-oxo-8-chloro-HPI
2-(3-aminobenzoyl)-4-oxo-9-methyl-HPI
2-(3-aminobenzoyl)-4-oxo-9-amino-HPI
2-(3-aminobenzoyl)-4-oxo-9-fluoro-HPI
2-(3-aminobenzoyl)-4-oxo-9-chloro-HPI
2-(3-aminobenzoyl)-4-oxo-10-methyl-HPI
2-(3-aminobenzoyl)-4-oxo-10-amino-HPI
2-(3aminobenzoyl)-4-oxo-10-fluoro-HPI
2-(3-aminobenzoyl)-4-oxo-10-chloro-HPI
2-(3-aminobenzoyl)-4-oxo-11-methyl-HPI
2-(3-aminobenzoyl)-4-oxo-11-amino-HPI
2-(3-aminobenzoyl)-4-oxo-11-fluoro-HPI
2-(3-aminobenzoyl)-4-oxo-11-chloro-HPI
2-(3-aminobenzoyl)-4-oxo-11b-methyl-HPI
1-methyl-2-(4-aminobenzoyl)-4-oxo-HPI
2-(4-aminobenzoyl)-3-methyl-4-oxo-HPI
2-(4-aminobenzoyl)-4-oxo-6-cis-methyl-HPI, ethanol solvate, m.p. 226° C.
2-(4-aminobenzoyl)-4-oxo-6-trans-methyl HPI
2-(4-aminobenzoyl)-4-oxo-7-methyl-HPI
2-(4-aminobenzoyl)-4-oxo-8-methyl-HPI
2-(4-aminobenzoyl)-4-oxo-8-amino-HPI
2-(4-aminobenzoyl)-4-oxo-8-fluoro-HPI
2-(4-aminobenzoyl)-4-oxo-8-chloro-HPI
2-(4-aminobenzoyl)-4-oxo-9-methyl-HPI
2-(4-aminobenzoyl)-4-oxo-9-amino-HPI
2-(4-aminobenzoyl)-4-oxo-9-fluoro-HPI
2-(4-aminobenzoyl)-4-oxo-9-chloro-HPI
2-(4-aminobenzoyl)-4-oxo-10-methyl-HPI
2-(4-aminobenzoyl)-4-oxo-10-amino-HPI
2-(4-aminobenzoyl)-4-oxo-10-fluoro-HPI
2-(4-aminobenzoyl)-4-oxo-10-chloro-HPI
2-(4-aminobenzoyl)-4-oxo-11-methyl-HPI
2-(4-aminobenzoyl)-4-oxo-11-amino-HPI
2-(4-aminobenzoyl)-4-oxo-11-fluoro-HPI
2-(4-aminobenzoyl)-4-oxo-11-chloro-HPI
2-(4-aminobenzoyl)-4-oxo-11b-methyl-HPI
2-(3-aminobenzoyl)-4-thioxo-HPI
2-(4-aminobenzoyl)-4-thioxo-HPI
2-(4-methylaminobenzoyl)-4-thioxo-HPI
2-(4-n-butylaminobenzoyl)-4-thioxo-HPI c. A solution of 4.9 g. 2-cyclohexylcarbonyl-4-oxo-8(or 11)-amino-HPI and 1.5 g. 35% formaldehyde solution in 200 ml. methanol is hydrogenated in the presence of 1 g. 5% palladium charcoal at 20° C. and at atospheric pressure. Subsequently, the reaction mixture is filtered and evaporated and the residue is purified by chromatographing over silica gel, using chloroform as elution agent. There is obtained 2-cyclohexylcarbonyl-4-oxo-8(or 11)-methyl-amino-HPI.

The following compounds are obtained analogously from the appropriate primary amines:

2-cyclohexylcarbonyl-4-oxo-11(or 8)-methylamino-HPI
2-(3-methylaminobenzoyl)-4-oxo-6-cis-methyl-HPI
2-(3-methylaminobenzoyl)-4-oxo-6-trans-methyl-HPI
2-(4-methylaminobenzoyl)-4-oxo-6-cis-methyl-HPI d. In a manner analogous to that described in c) above, from 4.9 g. 2-cyclohexylcarbonyl-4-oxo-8(or 11)-amino-HPI and 4 g. 33% formaldehyde solution, there is obtained 2-cyclohexylcarbonyl-4-oxo-8(or 11)-dimethylamino-HPI.

The following compounds are obtained analogously from the corresponding primary or secondary amines:

2-cyclohexylcarbonyl-4-oxo-11(or 8)-dimethylamino-HPI
2-(3-dimethylaminobenzoyl)-4-oxo-6-cis-methyl-HPI
2-(3-dimethylaminobenzoyl)-4-oxo-6-trans-methyl-HPI
2-(4-dimethylaminobenzoyl)-4-oxo-6-cis-methyl-HPI e. Over a period of 2 hours, 3.3 g. 2-cyclohexylcarbonyl-4-oxo-8(or 11)-amino-HPI in 100 ml. dioxane are mixed with 2.5 g. dimethyl sulfate and the reaction mixture substantially stirred at 100° C. for 15 hours. 1.4 g. potassium hydroxide in 5 ml. water are then stirred into the cooled solution. After the usual working up, there is obtained 2-cyclohexylcarbonyl-4-oxo-8(or 11)-dimethylamino-HPI.

In an analogous manner, with the use of diethyl sulfate and n-butyl bromide, there are obtained the following compounds:

2-cyclohexylcarbonyl-4-oxo-8(or 11)-dimethylamino-HPI
2-cyclohexylcarbonyl-4-oxo-8(or 11)-di-n-butylamino-HPI.

f. 4.2 g. 2-cyclohexylcarbonyl-4-oxo-8(or 11)-trifluoroacetamido-HPI (preferable by the reaction of 2-cyclohexylcarbonyl-4-oxo-8(or 11)-amino-HPI with trifluoroacetic anhydride/triethylamine in dichloromethane) are heated with 11.4 g. methyl iodide in 100 ml. dry acetone almost to boiling. 4.5 g. pulverized potassium hydroxide are then added thereto, followed by heating to the boil for 5 minutes, whereafter the reaction mixture is evaporated, the residue is mixed with water, stirred for 2 hours at 20° C. and then worked up as usual to give 2-cyclohexylcarbonyl-4-oxo-8(or 11)-methylamino-HPI.

If the methyl iodide is not removed before the hydrolysis, then there is obtained 2-cyclohexylcarbonyl-4-oxo-8(or 11)-dimethylamino-HPI.

g. 9.8 g. 2-cyclohexylcarbonyl-4-oxo-8(or 11)-amino-HPI and 1.5 g. formic acid in 100 ml. toluene are heated for 5 hours, with a water separator, then evaporated to dryness and, after trituration of the residue with diethyl ether, there is obtained 2-cyclohexylcarbonyl-4-oxo-8(or 11)-formamido-HPI.

h. 2.4 g. acetyl chloride in 50 ml. chloroform are added to 9.8 g. 2-cyclohexylcarbonyl-4-oxo-8(or 11)-amino-HPI and 3.1 g. triethylamine in 300 ml. chloroform and the reaction mixture is heated for 3 hours and then worked up as usual to give 2-cyclohexylcarbonyl-4-oxo-8(or 11)-acetamido-HPI.

The following compounds are obtained in an analogous manner with propionyl chloride and butyryl chloride:

2-cyclohexylcarbonyl-4-oxo-8(or 11)-propionamido-HPI
2-cyclohexylcarbonyl-4-oxo-8(or 11)-butyramido-HPI.

i. The diazonium fluoroborate prepared from 3.3 g 2-cyclohexylcarbonyl-4-oxo-8(or 11)-amino-HPI, 8 ml. 35% tetrafluoroboric acid, 0.7 g. sodium nitrite and 4 ml. water is filtered off, washed with 5% tetrafluoroboric acid, with a little ethanol and with diethyl ether, dried and decomposed at 130°–150° C. There is obtained 2-cyclohexylcarbonyl-4-oxo-8(or 11)-fluoro-HPI. Mass spectrum: m/e = 219; 330.

j. The aqueous suspension of the diazonium fluoroborate obtained according to (i) above is irradiated with a high pressure mecury lamp until the evolution of gas is finished. The reaction mixture is then extracted with chloroform and again there is obtained 2-cyclohexylcarbonyl-4-oxo-8(or 11)-fluoro-HPI.

k. 2.5 g. 2-cyclohexylcarbonyl-4-oxo-8(or 11)-amino-HPI are diazotised in 3 ml. 25% hydrochloric acid at about 0°–5° C. with a solution of 0.52 g. sodium nitrite in 3 ml. water. The diazonium solution is added dropwise, with stirring, to a mixture of 1 g. cuprous chloride in 4 ml. concentrated hydrochloric acid. The reaction mixture is slowly heated to about 90° C. until the evolution of gas has finished, followed by cooling, extraction with chloroform and purification of the organic phase chromatographically on silica gel to give 2-cyclohexylcarbonyl-4-oxo-8(or 11)-chloro-HPI; mass spectrum: m/e = 235; 346.

l. A diaxonium solution prepared from 3.3 g. 2-cyclohexylcarbonyl-4-oxo-8(or 11)-amino-HPI, 1.4 ml. concentrated sulfuric acid, 5 ml. water and 0.87 g. sodium nitrite is added, with stirring, to a solution of 4 g. potassium cyanide and 3.4 g. copper sulfate in 40 ml. water, buffered with 3.5 g. sodium bicarbonate. The reaction mixture is left to stand for half an hour and then worked up as usual to give 2-cyclohexylcarbonyl-4-oxo-8(or 11)-cyano-HPI; mass spectrum: m/e = 226; 337.

m. 2.5 g. 2-cyclohexylcarbonyl-4-oxo-8(or 11)-amino-HPI are dissolved in 3 ml. 25% hydrochloric acid and a solution of 0.52 g. sodium nitrite in 3 ml. water added thereto. The diazonium salt solution is introduced with stirring, into 50 ml. boiling water. Subsequently, it it boiled for 30 minutes and then worked up as usual to give 2-cyclohexylcarbonyl-4-oxo-8(or 11)-hydroxy-HPI.

The following compounds are obtained in an analogous manner:

2-cyclohexylcarbonyl-4-oxo-11(or 8)-hydroxy-HPI
2-(3-hydroxybenzoyl)-4-oxo-6-cis-methyl-HPI
2-(3-hydroxybenzoyl)-4-oxo-6-trans-methyl-HPI
2-(4-hydroxybenzoyl)-4-oxo-6-cis-methyl-HPI n. A diazonium salt solution prepared from 3.3 g. 2-cyclohexylcarbonyl-4-oxo-8(or 11)-amino-HPI, 5 ml. 6N hydrochloric acid, 0.7 g. sodium nitrite and 4 ml. water is allowed to run into a solution of 1.4 g. salicyclic acid in 15 ml. 2N aqueous hydroxide solution at 5°–10° C. After 30 minutes, the product obtained is precipitated out with hydrochloric acid, filtered off, washed with water and a little ethanol and dried. There is obtained orange-red 2-cyclohexylcarbonyl-4-oxo-8(or 11)-(3-carboxy-4-hydroxyphenylazo)-HPI.

The following compounds are obtained in an analogous manner with dimethylaniline, 2-naphthol-6-sulfonic acid and 2-methylanisole:

2-cyclohexylcarbonyl-4-oxo-8(or 11)-(4-dimethylaminophenylazo)-HPI
2-cyclohexylcarbonyl-4-oxo-8(or 11)-(2-hydroxy-6-sulpho-1-naphthylazo)-HPI
2-cyclohexylcarbonyl-4-oxo-8(or 11)-3-methyl-4-methoxyphenylazo-HPI.

The following compounds are also obtained in an analogous manner from diazotised 2-(3-aminobenzoyl)-4-oxo-6-trans-methyl-HPI with phenol or methylaniline:

2-(3-p-hydroxyphenylazobenzoyl)-4-oxo-6-trans-methyl-HPI
2-(3-p-methylaminophenylazobenzoyl)-4-oxo-6-trans-methyl-HPI

EXAMPLE 15 a. 20.2 g. 4-oxo-HPI in 500 ml. dioxan are heated to the boil and 20 g. phosphorus pentasulfide are added thereto portionwise within the course of 2 hours. The reaction mixture is heated for a further hour, the solvent is then removed and the residue is worked up as usual. The residue obtained is purified chromatographically over silica gel, using chloroform/methanol (95:5) as elution agent. There is obtained 4-thioxo-HPI which, after recrystallization from benzene, melts at 151° C.

In an analogous manner, with excess phosphorus pentasulfide, there is obtained from 2-cyclohexylcarbonyl-4-oxo-HPI, 2-cyclohexylthiocarbonyl-4-thioxo-HPI and from 2-benzoyl-4-oxo-HPI, 2-thiobenzoyl-4-thioxo-HPI.

b. 1.6 g. benzoyl chloride in 50 ml. chloroform are added to a solution of 2.2 g. 4-thioxo-HPI and 1.1 g. triethylamine in 100 ml. chloroform and the reaction mixture is stirred for an hour at 20° C. After the usual working up, there is obtained 2-benzoyl-4-thioxo-HPI which, after recrystallization from ethanol, melts at 184° C.

The following compounds are obtained analogously with the use of the appropriate acid chlorides:

2-acetyl-4-thioxo-HPI
2-cyclopentylcarbonyl-4-thioxo-HPI
2-cyclohexylcarbonyl-4-thioxo-HPI
2-cycloheptylcarbonyl-4-thioxo-HPI 2-(4-oxo-cyclohexyl-carbonyl)-4-thioxo-HPI
2-(tetrahydropyranyl-4-carbonyl)-4-thioxo-HPI
2-(tetrahydrothiopyranyl-4-carbonyl)-4-thioxo-HPI
2-(1-oxo-1-thiacyclohexyl-4-carbonyl)-4-thioxo-HPI
2-(1,1-dioxo-1-thiacyclohexyl-4-carbonyl)-4-thioxo-HPI
2-(3-fluorobenzoyl)-4-thioxo-HPI
2-(4-fluorobenzoyl)-4-thioxo-HPI
2-(3-chlorobenzoyl)-4-thioxo-HPI
2-(4-chlorobenzoyl)-4-thioxo-HPI
2-(3-nitrobenzoyl)-4-thioxo-HPI
2-(4-nitrobenzoyl)-4-thioxo-HPI
2-(4-dimethylaminobenzoyl)-4-thioxo-HPI
12-(4-di-n-butylaminobenzoyl)-4-thioxo-HPI 2-(4-formamidobenzoyl)-4-thioxo-HPI
2-(4-butyramidobenzoyl)-4-thioxo-HPI
2-(2-thienylcarbonyl)-4-thioxo-HPI
2-(3-thionylcarbonyl)-4-thioxo-HPI
2-(2-pyridylcarbonyl)-4-thioxo-HPI
2-nicotinoyl-4-thioxo-HPI
2-isonicotinoyl-4-thioxo-HPI

EXAMPLE 16.

6.4 g. S-thiobenzoyl-mercaptoacetic acid in 15 ml. 2N aqueous sodium hydroxide solution is added to 6.06 g. 4-oxo-HPI in 150 ml. tetrahydrofuran and the reaction mixture stirred for 12 hours at 20° C. The reaction mixture is worked up as usual to give 2-thiobenzoyl-4-oxo-HPI which, after recrystallization from ethanol/petroleum ether, melts at 98°–99° C.

The following compounds are obtained in an analogous manner by the thioacylation of the appropriate compounds which are unsubstituted in the 2-position:

(+)-2-thiobenzoyl-4-oxo-HPI; m.p. 167°–168° C.; $[\alpha]_D^{20} = + 56.1°$
1-methyl-2-thiobenzoyl-4-oxo-HPI
2-thiobenzoyl-3-methyl-4-oxo-HPI
2-thiobenzoyl-4-thioxo-HPI
2-thiobenzoyl-4-oxo-6-cis-methyl-HPI; m.p. 100°–101° C.
2-thiobenzoyl-4-oxo-6-trans-methyl-HPI
2-thiobenzoyl-4-oxo-7-methyl-HPI
2-thiobenzoyl-4-oxo-8-methyl-HPI
2-thiobenzoyl-4-oxo-9-methyl-HPI
2-thiobenzoyl-4-oxo-10-methyl-HPI
2-thiobenzoyl-4-oxo-11-methyl-HPI
2-thiobenzoyl-4-oxo-11b-methyl-HPI
2-(3-fluorothiobenzoyl)-4-oxo-HPI
1-methyl-2-(3-fluorothiobenzoyl)-4-oxo-HPI
2-(3-fluorothiobenzoyl)-3-methyl-4-oxo-HPI
2-(3-fluorothiobenzoyl)-4-thioxo-HPI
2-(3-fluorothiobenzoyl)-4-oxo-6-cis-methyl-HPI
2-(3-fluorothiobenzoyl)-4-oxo-6-trans-methyl-HPI
2-(3-fluorothiobenzoyl)-4-oxo-7-methyl-HPI
2-(3-fluorothiobenzoyl)-4-oxo-8-methyl-HPI
2-(3-fluorothiobenzoyl)-4-oxo-9-methyl-HPI
2-(3-fluorothiobenzoyl)-4-oxo-10-methyl-HPI
2-(34-fluorothiobenzoyl)-4-oxo-11-methyl-HPI
2-(3-fluorothiobenzoyl)-4-oxo-11b-methyl-HPI
2-(4-fluorothiobenzoyl)-4-oxo-HPI
1-methyl-2-(4-fluorothiobenzoyl)-4-oxo-HPI
2-(4-fluorothiobenzoyl)-3-methyl-4-oxo-HPI
2-(4-fluorothiobenzoyl)-4-thioxo-HPI
2-(4-fluorothiobenzoyl)-4-oxo-6-cis-methyl-HPI
2-(4-fluorothiobenzoyl)-4-oxo-6-trans-methyl-HPI
2-(4-fluorothiobenzoyl)-4-oxo-7-methyl-HPI
2-(4-fluorothiobenzoyl)-4-oxo-8-methyl-HPI
2-(4-fluorothiobenzoyl)-4-oxo-9-methyl-HPI
2-(4-fluorothiobenzoyl)-4-oxo-10-methyl-HPI
2-(4-fluorothiobenzoyl)-4-oxo-11-methyl-HPI
2-(4-fluorothiobenzoyl)-4-oxo-11b-methyl-HPI

EXAMPLE 17

6.06 g. 4-oxo-HPI and 2.5 g. thioacetamide are heated, while stirring, for 3 hours at 140° C. After the usual working up of the reaction mixture, there is obtained 2-thioacetyl-4-oxo-HPI which, after recrystallization from ethanol, melts at 133° C.

The following compounds are obtained in an analogous manner from the appropriate thioamides and the appropriate compounds unsubstituted in the 2-position:

2-cyclohexylthiocarbonyl-4-oxo-HPI; m.p. 180°–181° C.
2-cyclohexylthiocarbonyl-3-methyl-4-oxo-HPI
2-cyclohexylthiocarbonyl-4-oxo-6-cis-methyl-HPI
2-cyclohexylthiocarbonyl-4-oxo-6-trans-methyl-HPI
2-cyclohexylthiocarbonyl-4-oxo-7-methyl-HPI  2-cyclohexylthiocarbonyl-4-oxo-8-methyl-HPI
2-cyclohexylthiocarbonyl-4-oxo-9-methyl-HPI
2-cyclohexylthiocarbonyl-4-oxo-10-methyl-HPI
2-cyclohexylthiocarbonyl-4-oxo-11-methyl-HPI
2-cyclohexylthiocarbonyl-4-oxo-11b-methyl-HPI
2-(pyridyl-3-thiocarbonyl)-4-oxo-HPI; m.p. 158° C.
2-(pyridyl-3-thiocarbonyl)-3-methyl-4-oxo-HPI
2-(pyridyl-3-thiocarbonyl)-4-oxo-6-cis-methyl-HPI
2-(pyridyl-3-thiocarbonyl)-4-oxo-6-trans-methyl-HPI
2-(pyridyl-3-thiocarbonyl)-4-oxo-7-methyl-HPI
2-(pyridyl-3-thiocarbonyl)-4-oxo-8-methyl-HPI
2-(pyridyl-3-thiocarbonyl)-4-oxo-9-methyl-HPI
2-(pyridyl-3-thiocarbonyl)-4-oxo-10-methyl-HPI
2-(pyridyl-3-thiocarbonyl)-4-oxo-11-methyl-HPI
2-(pyridyl-3-thiocarbonyl)-4-oxo-11b-methyl-HPI
2-(pyridyl-4-thiocarbonyl)-4-oxo-HPI; m.p. 190° C.
2-(pyridyl-4-thiocarbonyl)-3-methyl-4-oxo-HPI
2-(pyridyl-4-thiocarbonyl)-4-oxo-6-cis-methyl-HPI
2-(pyridyl-4-thiocarbonyl)-4-oxo-trans-methyl-HPI
2-(pyridyl-4-thiocarbonyl)-4-oxo-7-methyl-HPI
2-(pyridyl-4-thiocarbonyl)-4-oxo-8-methyl-HPI
2-(pyridyl-4-thiocarbonyl)-4-oxo-9-methyl-HPI
2-(pyridyl-4-thiocarbonyl)-4-oxo-10-methyl-HPI
2-(pyridyl-4-thiocarbonyl)-4-oxo-11-methyl-HPI
2-(pyridyl-4-thiocarbonyl)-4-oxo-11b-methyl-HPI.

EXAMPLE 18

3.7 g. cyclohexyl chloroformate in 20 ml. dichloromethane are added at 20° C. to a solution of 4.04 g. 4-oxo-HPI and 2 g. triethylamine in 80 ml. dichloromethane and the reaction mixture then stirred for an hour at 20° C. After the usual working up, there is obtained 2-cyclohexyloxycarbonyl-4-oxo-HPI, which melts at 105°–106° C.

The following compounds are obtained in an analogous manner, with the use of the appropriate chloroformic acid esters:

2-methoxycarbonyl-4-oxo-HPI
2-ethoxycarbonyl-4-oxo-HPI; m.p. 78° C.
2-ethoxycarbonyl-3-methyl-4-oxo-HPI
2-ethoxycarbonyl-4-oxo-6-cis-methyl-HPI
2-ethoxycarbonyl-4-oxo-6-trans-methyl-HPI
2-ethoxycarbonyl-4-oxo-7-methyl-HPI
2-ethoxycarbonyl-4-oxo-8-methyl-HPI
2-ethoxycarbonyl-4-oxo-9-methyl-HPI 2-ethoxycarbonyl-4-oxo-10-methyl-HPI
2-ethoxycarbonyl-4-oxo-11-methyl-HPI
2-ethoxycarbonyl-4-oxo-11b-methyl-HPI
2-n-propoxycarbonyl-4-oxo-HPI
2-n-butoxycarbonyl-4-oxo-HPI
2-cyclopentyloxycarbonyl-4-oxo-HPI
2-cyclohexyloxycarbonyl-3-methyl-4-oxo-HPI
2-cyclohexyloxycarbonyl-4-oxo-6-cis-methyl-HPI
2-cyclohexyloxycarbonyl-4-oxo-6-trans-methyl-HPI
2-cyclohexyloxycarbonyl-4-oxo-7-methyl-HPI
1-cyclohexyloxycarbonyl-4-oxo-8-methyl-HPI
2-cyclohexyloxycarbonyl-4-oxo-9-methyl-HPI
2-cyclohexyloxycarbonyl-4-oxo-10-methyl-HPI
2-cyclohexyloxycarbonyl-4-oxo-11-methyl-HPI
2-cyclohexyloxycarbonyl-4-oxo-11b-methyl-HPI
2-cyclohexyloxycarbonyl-4-oxo-HPI
2-phenoxycarbonyl-4-oxo-HPI; m.p. 136°–137° C.

The parasitological action of the new compounds according to the present invention is described in more detail in the following:

EXAMPLE OF USE

Action against *Hymenolepis nana* (in mice), *Hymenolepis microstoma* (in mice) and *Hymenolepis diminuta* (in rats).

Experimental animals which had been infected with *H. nana*, *H. microstoma* or *H. diminuta* were treated after the expiry of the prepatence of the parasites. The active compound used was administered orally or subcutaneously as an aqueous suspension.

The degree of action of the preparation was determined in that, after sacrifice of the experimental animal, the remaining worms were counted, in comparison with untreated control animals, from which was calculated the percentage activity.

The compounds set out in the following Table show the indicated effectiveness against the above-mentioned parasites:

TABLE

| Active Compound | parasite | Effective minimum dosage in mg/kg (parasite reduction > 90%) |
|---|---|---|
| 2-benzoyl-4-oxo-6-trans-methyl-HPI | H. nana | 25 |
|  | H. microstoma | 50 |
|  | H. diminuta | 50 |
| 2-benzoyl-4-oxo-6-cis-methyl-HPI | H. nana | 50 |
| 2-benzoyl-4-oxo-7-methyl-HPI | H. nana | 25 |
| 2-(4-aminobenzoyl)-4-oxo-6-cis-methyl-HPI | H. nana | 50 |
|  | H. microstoma | 50 |
| 2-(3-nitrobenzoyl)-4-oxo-6-cis-methyl-HPI | H. nana | 50 |
| 2-cyclohexylcarbonyl-4-oxo-6-trans-methyl-HPI | H. nana | 50 |
|  | H. microstoma | 50 |
|  | H. diminuta | 50 |
| 2-cyclohexylcarbonyl-4-oxo-8(or 11)-amino-HPI | H. nana | 50 |
| 2-(cyclohex-3-en-yl-carbonyl)-4-oxo-6-cis-methyl-HPI | H. nana | 50 |
| 2-thiobenzoyl-4-oxo-HPI | H. nana | 50 |
|  | H. microstoma | 50 |
|  | H. diminuta | 50 |
| 2-(pyridyl-3-thio-carbonyl)-4-oxo-HPI | H. nana | 50 |
| Quinacrine | H. diminuta | >1000 |
| Miclosamide | H. nana | 500 |
|  | H. microstoma | 500 |
| Dichlorophen | H. nana | >1000 |
|  | H. diminuta | 500 |

The active materials of general Formula I can be formulated into pharmaceutical compositions according to the methods known from the literature, as the following Examples demonstrate:

EXAMPLE A

Tablets for combating cestodes (adult)

a. Tablets containing 500 mg. 2-benzoyl-4-oxo-7-methyl-HPI as active compound are prepared by working up a powder mixture which consists of 5 kg. 2-benzoyl-4-oxo-7-methyl-HPI, 3-kg. lactose, 1.8 kg. maize starch and 0.2 kg. magnesium stearate.

b. The same mixture can be used for the production of tablets which contain 50, 250 and 1000 mg. 2-benzoyl-4-oxo-7-methyl-HPI.

The tablets containing 250 and 500 mg. 2-benzoyl-4-oxo-7-methyl-HPI as active compound are preferably used for human medicine. All of the above-mentioned tablets can be used for veterinary medicinal purposes.

EXAMPLE B.

Tablets preferable for combating cestode hydatids and Schistosomes a. Effervescent tablets
Each tablet contains:

| | |
|---|---|
| 2-benzoyl-4-oxo-7-methyl-HPI | 1000 mg. |
| citric acid | 800 mg. |
| sodium carbonate | 900 mg. |
| saccharin | 5 mg. |
| saccharose | ad 4000 mg. | b. Sugared chewing tablets
Each tablet contains:

| | |
|---|---|
| 2-benzoyl-4-oxo-7-methyl-HPI | 2000 mg. |
| cellulose | 80 mg. |
| sodium carboxymethylcellulose | 40 mg. |
| coloring and aroma materials | as desired |
| saccharose | ad 4000 mg. |

EXAMPLE C

Dragees for combating cestodes in human medicine

Each dragee core contains:

| | |
|---|---|
| 2-benzoyl-4-oxo-7-methyl-HPI | 250 mg. |
| lactose | 150 mg. |
| maize starch | 90 mg. |
| magnesium stearate | 10 mg. |

The dragee coating consists of talc, saccharose, titanium dioxide, calcium carbonate, polyvinyl-pyrrolidone, methyl cellulose, glycerol, magnesium oxide and lacquer.

This formulation can also be used for dragees which contain 500 mg. 2-benzoyl-4-oxo-7-methyl-HPI as active compound.

EXAMPLE D

Syrup for combating cestodes (human medicine)

The syrup is made by preparing a suspension of:

| | |
|---|---|
| 2-benzoyl-4-oxo-7-methyl-HPI | 3.5 kg. |
| distilled water | 2 liters |
| buffer | 0.1 liters |
| glycerol | 3 kg. |
| sorbitol | 3 kg. |
| saccharose | 53 kg. |
| mixture of 60% methyl p-hydroxy- | |

| | |
|---|---|
| benzoate and 40% propyl p-hydroxy-benzoate | 0.1 kg. |
| ethanol | 12 liters |

The mixture is admixed with coloring and aroma materials and made up to 100 liters with distilled water.

EXAMPLE E

Capsules for combating cestodes and Schistosomes in human and veterinary medicine.

Capsules of appropriate size are filled with a mixture of:

| | |
|---|---|
| 2-benzoyl-4-oxo-7-methyl-HPI | 5000 mg. |
| talc | 250 mg. |
| magnesium stearate | 150 mg. |

Capsules containing 1000 mg. and 10,000 mg. of the active compound are prepared in the same way.

EXAMPLE F

Injection liquid for human and veterinary medicinal purposes.

For subcutaneous administration in oily or aqueous suspension, 15 mg. ampoules are filled with a solution of 500 mg. 2-benzoyl-4-oxo-7-methyl-HPI in 6 ml. water and 4 ml. propylene glycol, with the addition of a solubilizing agent. The ampoules are heat-sterilized or are provided with a preservation agent.

Similar ampoules are produced containing 100 mg. 2-benzoyl-4-oxo-7-methyl-HPI (for small animals) and 1000 mg. 2-benzoyl-4-oxo-7-methyl-HPI (for large animals).

EXAMPLE G

Pellets

A powder mixture is produced from equal parts by weight of 2-benzoyl-4-oxo-7-methyl-HPI and lactose which mixture, together with sodium carboxymethylcellulose, is worked up in the usual manner to give a uniform granulate with an average particle size of 1.5 mm.

EXAMPLE H

Veterinary medicinal pre-mixture which is suitable, with a feedstuff as carrier, for further mixing to a medicated feed.

a. 25% pre-mixture (preferably for larger animals)

25 kg. 2-benzoyl-4-oxo-7-methyl-HPI are mixed with 75 kg. fine bran (wheat after millings) and/or lactose.

b. 5% pre-mixture (preferably for smaller animals)

5 kg. 2-benzoyl-4-oxo-7-methyl-HPI are worked up in a manner analogous to (a) above.

c. Example of a use of the pre-mixture according to a) above for combating Moniezia types in bovine intestines.

In order to obtain a suitable medicated feed, 1 kg. of the pre-mixture produced according to a) above is mixed with 9 kg. of a conventional feed concentrate. 400 g. of this medicated feed, containing 10,000 mg. 2-benzoyl-4-oxo-7-methyl-HPI are administered for combating Moniezia infection in adult cattle.

Analogously to Examples A to H, instead of 2-benzoyl-4-oxo-7-methyl-HPI, there can also be used the other active materials for general formula (I) or other physiologically compatible acid-addition salts for the preparation of pharmaceutical compositions.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

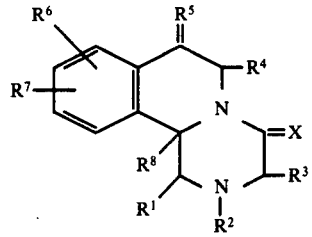

wherein $R^1$ is a hydrogen atom, hydroxy or alkyl; $R^2$ is

$R^3$ is a hydrogen atom, alkyl or hydroxyalkyl; $R^4$ is a hydrogen atom, alkyl or phenyl; $R^5$ is an oxygen atom, two hydrogen atoms, or a hydrogen atom and one of alkyl, phenyl, halogen atoms, or hydroxy; $R^6$ and $R^7$, which can be alike or different, each are a hydrogen atom, a halogen atom, hydroxy, amino, nitro, cyano, alkyl, alkoxy, alkanoyloxy, monoalkylamino, dialkylamino, alkanoylamino, or benzoyloxy; $R^8$ is a hydrogen atom or alkyl; $R^9$ is cycloalkyl or cycloalkenyl of 5 to 7 carbon atoms which is unsubstituted or, substituted by a carbonyl oxygen atom X and Y, which can be the same or different, each is an oxygen or sulfur atom; with the proviso that $R^2$ is

when $R^1$ and $R^3$ to $R^8$, inclusive, each are hydrogen atoms and X is an oxygen atom alkyl, hydroxyalkyl, alkoxy and alkanoyl being up to 4 carbon atoms.

2. The compound of claim 1, 2-cyclohexylcarbonyl-4-oxo-6-trans-methyl-1,2,3,6,7,11b-hexahydro-4H-pyrazino[2,1-a]isoquinoline.

3. The compound of claim 1, 2-cyclohexylcarbonyl-4-oxo-8(or 11)-amino-1,2,3,6,7,11b-hexahydro-4H-pyrazino[2,1-a]isoquinoline.

4. The compound of claim 1, 2-cyclohexylcarbonyl-4-oxo-11b-methyl-1,2,3,6,7,11b-hexahydro-4H-pyrazino[2,1-a]isoquinoline.

5. A compound of claim 1 wherein $R^2$ is

and $R^9$ is cyclohexyl or cyclohexenyl.

6. A compound of claim 5 wherein $R^9$ is cyclohexyl.

7. A compound of claim 1 wherein $R^1$ is hydrogen, $R^3$ is hydrogen or methyl, $R^4$ is hydrogen or methyl, $R^5$ represents two hydrogen atoms, or a hydrogen atom and a methyl group, one of $R^6$ and $R^7$ is hydrogen and the other is hydrogen, amino, nitro or chlorine, $R^8$ is hydrogen and $R^9$ is cyclohexyl.

8. A compound of claim 1, 1-methyl-2-cyclohexylcarbonyl-4-oxo-1,2,3,6,7,11b-hexahydro-4H-pyrazino[2,1-a]isoquinoline.

9. A compound of claim 1, 2-cyclohexylcarbonyl-3-methyl-4-oxo-1,2,3,6,7,11b-hexahydro-4H-pyrazino[2,1-a]isoquinoline.

10. A compound of claim 1, 2-cyclohexylcarbonyl-4-oxo-6-cis-methyl-1,2,3,6,7,11b-hexahydro-4H-pyrazino[2,1-a]isoquinoline.

11. A compound of claim 1, 2-cyclohexylcarbonyl-4-oxo-7-methyl-1,2,3,6,7,11b-hexahydro-4H-pyrazino[2,1-a]isoquinoline.

12. A compound of claim 1, 2-cyclohexylcarbonyl-4-oxo-8(or 11)-amino-1,2,3,6,7,11b-hexahydro-4H-pyrazino[2,1-a]isoquinoline.

13. A compound of claim 1, 2-cyclohexylcarbonyl-4-oxo-8(or 11)-chloro-1,2,3,6,7,11b-hexahydro-4H-pyrazino[2,1-a]isoquinoline.

14. A compound of claim 1, 2-(cyclohexene-4-carbonyl)-4-oxo-6-trans-methyl-1,2,3,6,7,11b-hexahydro-4H-pyrazino[2,1-a]isoquinoline.

15. A compound of claim 1, 2-(cyclohexene-4-carbonyl)-4-oxo-11b-methyl-1,2,3,6,7,11b-hexahydro-4H-pyrazino[2,1-a]isoquinoline.

16. A compound of claim 1, 2-cyclohexyl-thiocarbonyl-4-oxo-1,2,3,6,7,11b-hexahydro-4H-pyrazino[2,1-a]isoquinoline.

17. An anthelmintic composition comprising an anthelmintically effective amount per unit dosage of at least one compound of claim 1 in admixture with a pharmaceutically acceptable carrier or in admixture with an animal feed or feed concentrate.

18. An anthelmintic composition according to claim 17 adapted for oral administration.

19. An anthelmintic composition according to claim 17, in capsule form.

20. A method of treating helminthiasis which comprises administering to the infested patient an anthelmintically effective amount of at least one compound of claim 1.

21. A method of claim 20 wherein the patient is human.

22. A method of claim 20 wherein the patient is animal.

* * * * *